(12) United States Patent
Postlethwaite et al.

(10) Patent No.: US 9,144,595 B2
(45) Date of Patent: Sep. 29, 2015

(54) APLS FOR TREATING ARTHRITIS

(71) Applicants: Arnold E. Postlethwaite, Eads, TN (US); Andrew Ho Kang, Memphis, TN (US); Linda K. Myers, Memphis, TN (US)

(72) Inventors: Arnold E. Postlethwaite, Eads, TN (US); Andrew Ho Kang, Memphis, TN (US); Linda K. Myers, Memphis, TN (US)

(73) Assignee: University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 14/043,444

(22) Filed: Oct. 1, 2013

(65) Prior Publication Data

US 2014/0113867 A1    Apr. 24, 2014

Related U.S. Application Data

(63) Continuation of application No. 12/914,823, filed on Oct. 28, 2010, now abandoned.

(60) Provisional application No. 61/255,627, filed on Oct. 28, 2009.

(51) Int. Cl.
*A61K 38/16* (2006.01)
*A61K 38/17* (2006.01)

(52) U.S. Cl.
CPC ............. *A61K 38/16* (2013.01); *A61K 38/1709* (2013.01)

(58) Field of Classification Search
CPC ........................... A61K 38/16; A61K 38/1709

USPC ........................................................ 514/16.6
See application file for complete search history.

(56) References Cited

U.S. PATENT DOCUMENTS

| | | | |
|---|---|---|---|
| 5,843,445 A | 12/1998 | Weiner et al. | |
| 6,468,537 B1 * | 10/2002 | Datta et al. | 424/185.1 |
| 7,074,415 B2 * | 7/2006 | Hamel et al. | 424/244.1 |
| 8,383,771 B2 * | 2/2013 | Horta et al. | 530/324 |
| 2002/0037844 A1 | 3/2002 | Myers et al. | |
| 2003/0148944 A1 | 8/2003 | Holmdaahl | |
| 2009/0171069 A1 * | 7/2009 | Dominguez Horta et al. | 530/324 |

OTHER PUBLICATIONS

Han H-K, "Targeted Prodrug Design to Optimize Drug Delivery," AAPS Pharmsci, 2000; 2(1): 1-11.*
International Search Report and Written Opinion for PCT/US2010/054532, mailed May 16, 2011, 10 pgs.
Barnett et al., "A pilot trial of oral type II collagen in the treatment of juvenile rheumatoid arthritis", Arthritis & Rheumatism vol. 39, No. 4, pp. 623-628 (1996).
Bäcklund et al., "Glycosylation of type II collagen is of major importance for T cell tolerance and pathology in collagen-induced arthritis", Eur. J. Immunol. 32, pp. 3776-3784 (2002).

* cited by examiner

*Primary Examiner* — Julie Ha
(74) *Attorney, Agent, or Firm* — Squire Patton Boggs (US) LLP

(57) ABSTRACT

One embodiment of a therapeutic composition comprises one or more APLs, e.g., APL A12, for treating diseases or disorders related to arthritis, including rheumatoid arthritis. Another embodiment includes a method of inducing a Th2-type cytokine secretion profile in a mammal, including administering a therapeutic amount of A12 analog peptide. Another embodiment includes a method for generating functional T regulatory cells, the method including administering a therapeutic amount of APL A12 to a RA patient.

16 Claims, 10 Drawing Sheets

APLS FOR TREATING ARTHRITIS

CROSS-REFERENCE TO RELATED APPLICATIONS

This application is a continuation of U.S. patent application Ser. No. 12/914,823, filed Oct. 28, 2010, which claims the benefit of U.S. Provisional Patent Application No. 61/255,627 filed on Oct. 28, 2009, the content of which is incorporated herein by reference in its entirety.

TECHNICAL FIELD

APLs for treating arthritis relates to altered peptide ligands and their uses in relation to arthritis.

BACKGROUND OF THE INVENTION

Rheumatoid arthritis (RA) in most populations is highly associated with a set of alleles at the B1 locus of the HLA-DR region (HLA-DRB1 *0101, *0401, *0404, *0405, *1001, *0408, *1402, *0102 and *1303) called "shared epitope" alleles. The *0401 and *0404 alleles also called DR1 and DR4, respectively, on antigen presenting cells bind to a minimum dominant determinant on type II collagen (CII) residues 263-270 (FKGEQGPK)(SEQ ID NO: 1). Altered peptide ligands (APLs) are peptides that retain enough of the present sequence to be recognized by T cells in the MHC/peptide T cell receptor (TCR) trimolecular complex but interfere with normal signaling through the TCR. APLs can act as antagonists or partial agonists. In animal models, APLs have been shown to be effective in preventing and ameliorating tissue-specific autoimmune diseases. Trials of APL in human autoimmune disease have had mixed results. However, none of these trials incorporated a pre-selection step wherein the APL showed ability in vitro to down regulate Th1 response by patient's peripheral blood mononuclear cells (PBMC) stimulated by an autoantigen as described by herein.

Collagen Autoimmunity in RA

Autoimmunity plays a central role in a diverse group of diseases that afflict man, including rheumatoid arthritis (RA). This systemic disease is characterized by chronic synovitis, which shows a predilection for diarthrodial joints. If unchecked, the synovial inflammation typically produces irreversible joint destruction and permanent disability. A preponderance of evidence indicates that an antigen-driven immune process against one or more proteins found in cartilage sustains synovial inflammation in RA. Although several antigens have been proposed to be involved in the autoimmune response in RA, CII has received the most attention as a candidate autoantigen. It is the predominant protein of articular cartilage, and autoimmunity to CII is common in patients with RA with >60% of RA patients having large amounts of anti-CII cartilage bound antibodies in arthritic joints. Mullazehi and colleagues have reported that autoimmunity to CII correlates with disease severity. RA patients with high serum levels of anti-CII antibodies have a distinct clinical phenotype characterized by an early acute phase response associated with more severe radiological damage in the joints at the time of diagnosis. Moreover, immune complexes from RA synovia, which contained anti-CII antibodies, induced the proinflammatory cytokine tumor necrosis factor (TNF)α and this induction directly correlated with the number of swollen and tender joints. Blockade of the monocyte receptor, Fc gamma RIIa, decreased TNFα production in the joints. These data demonstrate a direct link between the level of autoimmunity to CII and the severity of RA and in such patient's downregulation of autoimmunity to CII should lead to modulation of the destructive arthritis itself.

A form of CII based therapy has been tried in patients with RA and juvenile RA by administering intact native chick or bovine CII to patients. Seven trials of treatment with oral CII have been reported including two of our own. In each case, the native CII was well tolerated with no or mild adverse events. Two of the studies gave favorable results, demonstrating small, but significant, disease improvement. However, the therapeutic window was narrow, suggesting a need to fine-tune future trials of collagen-based therapy. Most patients in these studies also received NSAIDs which block oral tolerance and systemic tolerance. The use of NSAIDS might have been responsible for the mixed results of oral CII in RA. We have conducted studies in murine models of oral tolerance that show the PGE1 analog, misoprostol, reverses NSAID inhibition of oral tolerance and that DMARDs and the anti-TNFα biologic, etanercept, do not block oral tolerance induction. Furthermore, we have applied these crucial data in designing oral tolerance trials in humans. We can down regulate with oral CII, PBMC production of IFNγ to α1(II) in RA patients who take NSAIDS plus misoprostol and/or DMARDS and anti-TNFα therapies. Oral administration of low dose antigen generates regulatory T cells, which act in the respective microenvironment in a non-antigen specific manner by producing down-regulatory cytokines such as IL4, IL10 and TGFbeta, a Th2/Th3 cytokine pattern. Recent studies in mice show that orally administered antigen can induce $CD4^+$ $CD25^+$ Fox $P3^+$ regulatory T cells (Tregs) via retinoic acid dependent mechanisms.

Altered Peptide Ligands in the Treatment of Human Disease

APLs are analogs of determinants recognized by T cells in the MHC/peptide/TCR trimolecular complex. These altered peptides interfere with normal signaling through the TCR. The APL is bound by MHC but because it is presented differently than the naturally occurring epitope, it is recognized aberrantly. APL may act as antagonists or partial agonists. Studies in animal systems have shown that APLs are effective in preventing or ameliorating many tissue-specific autoimmune diseases. Based on the experience in animals, APLs should provide a relatively nontoxic and highly specific therapy for humans with tissue-specific autoimmune diseases. However, human trials have met with mixed results. Treatment of multiple sclerosis with peptide analogs of myelin basic protein administered subcutaneously resulted in an increase in disease activity. On the other hand, trials in type 1 diabetes and in RA have shown promising results. Raz and coworkers treated 35 subjects who had type 1 diabetes with peptide p277, a peptide analog from heat-shock protein hsp60. The treatment group received a total of three injections. After 10 months the treatment group had higher levels of C peptide and reduced need for exogenous insulin as compared to controls. Prakken and coworkers treated 15 patients with RA using a peptide analog of a heat-shock protein, dnaJP1, which shares sequence homology with the shared epitope. Subjects were treated orally with 3 different dosages for six months. Reactivity to dnaJP1 was significantly altered with a decrease in the number of cells producing IFN-γ and IL-2. There was a concomitant increase in IL-4 and IL-10 producing cells. Efficacy in producing a change in the clinical manifestations of disease was not determined due to the small number of patients studied.

We have shown that mice normally resistant to CIA that are transgenic for the human RA MHC susceptibility genes DR1 and DR4 develop arthritis after immunization with human CII. This arthritis can be prevented by administration of an APL that we have named A12. Although the precise mechanism by which the A12 peptide exerts its effect is not yet clear, the interaction of the APL/MHC complex with the TCR appears to play a key role in influencing the differentiation of naive T cells into effector cells.

When optimal engagement occurs between a TCR and a specific antigen in the context of a class II MHC molecule, signal transduction events are initiated. Minor variations in the physicochemical properties of amino acid residues of the peptide which interact with either MHC or TCR can lead to disparate immunological responses. For example, an APL containing a single amino acid substitution at the TCR contact residue of a cytochrome-C peptide has been shown to induce immune deviation to a Th2-type response as compared to the WT agonist peptide, which induced a Th1 response. A double APL based on 2 epitopes in acetylcholine recognized by patients with myasthenia gravis induced generation of CD4+ CD25+ FoxP3+ regulatory T cells and induced Fas dependent and Fas independent apoptosis of acetylcholine-specific T cells. A shift to a Th2 cytokine profile may be significant for the development of arthritis, because Th2 cytokines have inhibitory effects on CIA. IL-10 is effective in inhibiting CIA when administered to mice. IL-4 has a similar effect although it does not duplicate the effects of IL-10.

One of the fundamental and most challenging goals of immunological research is to devise a treatment that suppresses immunity enough to halt an injurious autoimmune process, without disrupting the beneficial functions of the immune system such as surveillance for opportunistic infections and tumors. To this end, analog (or altered) peptide ligands are particularly desirable types of antigen-specific immunotherapy and are well suited for treating autoimmune diseases. They can specifically down-regulate an inflammatory autoimmune response in diarthodial joints where CII is located. Although the use of APLs as therapies for human illness is still in its infancy, recent reports suggest that APLs can modulate autoimmune arthritis by inducing regulatory T cells.

Because RA is strongly associated with DR genes, it seems likely that immune-mediated mechanisms are critically involved, either in the initiation of disease or in its progression to severe joint destruction with systemic manifestations, or both. An antigen that could perpetuate an autoimmune-mediated response is CII. There is incontrovertible evidence that RA is characterized by autoimmunity to CII. Most patients with RA have local production of antibodies to CII in joint tissues. Similar antibodies have been found to be pathogenic in mice with CIA. In mice the autoantibody response is CD4 T cell driven and strongly associated with class II immune response genes including human DR4 and DR1. Other investigators have concluded, "The genetic associations between HLA-DR alleles and antibodies to CII in RA patients is in keeping with the collagen-induced arthritis model and implicates autoimmunity to CII as a major component in the multifactorial pathogenesis of RA". The ultimate test of that possibility is specifically altering the immune response to CII and determining its affect on disease. Using APLs described herein addresses these issues.

BRIEF SUMMARY OF THE INVENTION

This disclosure provides therapeutic compositions comprising one or more APLs, e.g., APL A12, for treating diseases or disorders related to arthritis, including rheumatoid arthritis. In one embodiment a therapeutic composition includes an altered peptide ligand (APL) for treatment or inhibition of Rheumatoid Arthritis (RA) in patients in need thereof. In another embodiment a method of making the therapeutic composition, including an altered peptide ligand (APL) for treatment or inhibition of Rheumatoid Arthritis (RA), includes genetic or non-genetic procedures. In another embodiment a method of inducing a Th2-type cytokine secretion profile in a mammal, comprising administering a therapeutic amount of A12 analog peptide. In another embodiment a method generating functional T regulatory cells, the method comprising administering a therapeutic amount of APL A12 to a RA patient.

This disclosure provides methods for determining APLs effective in treating diseases or disorders or disorders related to arthritis, including rheumatoid arthritis.

This disclosure provides methods of treating or inhibiting diseases or disorders related to arthritis, including rheumatoid arthritis, in a patient in need thereof. This disclosure provides methods of downregulating biological/physiological pathways that lead to diseases or disorders related to arthritis, including rheumatoid arthritis.

DETAILED DESCRIPTION OF THE INVENTION

Figure 1:
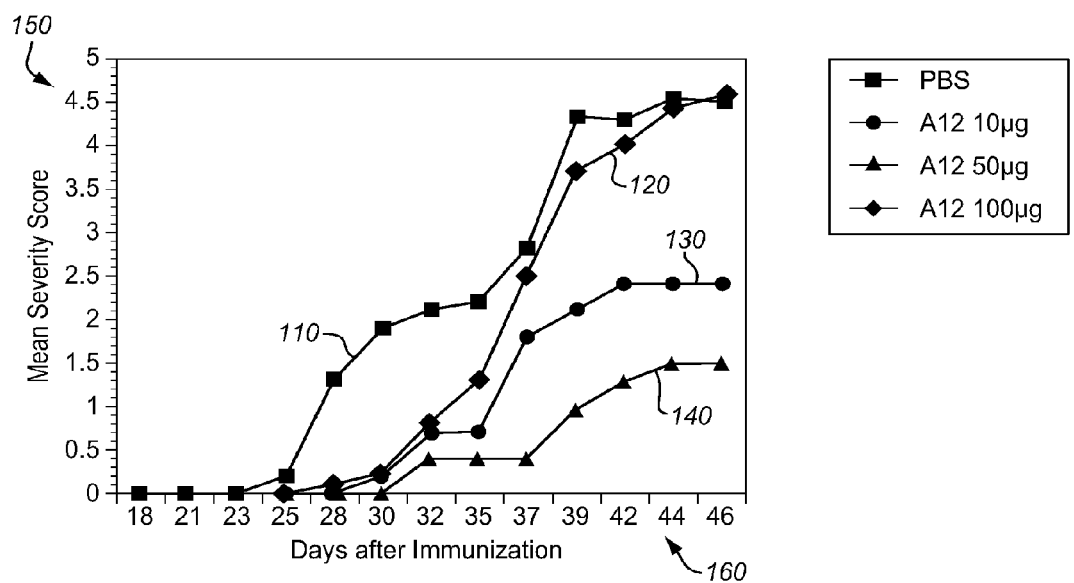
FIG. 1 shows arthritis severity in CII immunized DR1 transgenic mice.

This disclosure describes an APL based on the minimum dominant determinant on CII residues 263-270. The APL called HC Peptide1 (also called herein "APL A12", "A12 peptide", "A12 analog" or variations thereof) has the following amino acid sequence: LGPKGQTGEBGIAGAKGDQG-PKGEBGPA (SEQ ID NO: 2). Our preclinical studies using mice transgenic for the human DR1 allele shows that at low oral dose (10-50 µg) HC Peptide 1 protects the mice from development of arthritis induced by immunization with bovine CII, also known as the collagen-induced arthritis (CIA) model. Acute toxicity studies in mice show that oral administration of HC Peptide 1 at 100× the proposed human dose daily for six days was not associated with clinical signs of illness, changes in complete blood counts or liver and renal chemistries. Histologic examination of internal organs did not reveal abnormalities in mice given HC Peptide 1. In in vitro studies, we found that exogenously added HC Peptide 1 suppressed Th1 cytokine production by cultures of PBMC stimulated by the a1 chain of CII [α1(II)] from more RA patients who typed positive for one or more of the shared epitope alleles than from those who were shared epitope negative. Based on these encouraging preliminary data, we are submitting this initial investigational new drug application to conduct a Phase I dosing and toxicity study in patients with RA. We applied to the Department of Veterans Affairs and have secured funding to conduct this Phase I study.

While this disclosure provides specific embodiments, it will be understood that the APLs For Treating Arthritis can comprise desired APLs in formulations and doses of various compositions. Various doses and ranges of doses of APLs to be tested will include those specifically addressed herein, and include those doses and ranges found to effectively serve in or as therapeutic compositions for treating, inhibiting or ameliorating the diseases and disorders or the effects of diseases and disorders on patients in need thereof. The APLs described can be used with various compounds, including, but not limited to, carriers, excipients, solvents, fillers, delivery compounds, prodrugs, and various protecting groups, for example pegylation and glycosylation.

Methods of making the desired APLs includes those methods known to the artisan of ordinary skill within the art, including genetic and non-genetic procedures.

Identification of an APL Capable of Preventing Arthritis in DR Transgenic Mice

Assuming that $CII_{263-270}$ was key to developing immunity to the intact CII molecule, a number of analog peptides where amino acids within this small segment were substituted with those found in the corresponding sites of nonarthritogenic type I collagen were prepared and tested. It was found that the A12 analog containing substitutions made at positions 263 (F→N) and 266 (E→D) could profoundly suppress immunity to CII and arthritis in high-responder DR1 and DR4 mice. The APL A12 developed for this study has the following amino acid sequence: LGPKGQTGEBG[IAGNKGDQGPK]GE BGPA (SEQ ID NO: 3) where B=hydroxyproline. The core determinant of human $CII_{263-270}$ is bracketed. The underlined residues are those substituted to produce APL A12. The residues amino terminal and carboxy terminal to the core determinant is from the normal human CII sequence. When DR1-Transgenic mice were immunized with CII, CII plus A12, or CII plus a control peptide and observed for the development of arthritis, a dose-related decrease in the incidence of arthritis and number of arthritic limbs was observed. Concordant with a decrease in the incidence and severity of arthritis, antibody production to CII was also significantly decreased and APL A12 was effective even when administered after CII-immunization (Table I).

Mechanism of Action of APL A12.

One of the most important characteristics of the A12 analog peptide was its ability to induce a Th2-type cytokine secretion profile. In this set of experiments, DR1 transgenic mice were immunized with A12 peptide or CII emulsified with CFA. Culture of the immune T cells with various antigens showed that the cells from mice receiving A12 secreted predominantly Th2 cytokines in response to itself or α1(II) while their response to PPD was Th1. In contrast, cells from mice immunized with CII generated predominantly a Th1 response to the wild-type peptide. Together, these data suggest that a population of cells can be induced that respond to the A12 peptide with a predominantly Th2 phenotype. The ability to induce the secretion of Th2 cytokines may explain the profound suppressive effects A12 has on the development of CIA. A 21 mer peptide with the A12 263N and 266D substitution exhibited weakened binding to both DR1 and DR4 molecules (9 and 65). These data suggest competition of A12 with native CII for binding to DR1 and DR4.

APL A12 Suppresses CIA in DR1 Transgenic Mice when Given Orally

We wanted to determine whether APL A12 given orally would suppress CIA in DR1 transgenic mice. To assess this, groups of 10 DR1 transgenic mice were gavaged 8 days over two weeks with the following: PBS, 10 μg APL A12, 50 μg APL A12, or 100 μg APL A12. Mice were then immunized with 50 μg bovine CII in CFA, and arthritis severity was assessed as previously described. Two low doses of APL A12 significantly reduced arthritis severity, 50 μg and 10 μg (FIG. 1). Although the reason for this lower dose response is not apparent from this experiment, this better response to the 10 μg and 50 μg doses and compared to 100 μg is reminiscent of low dose native CII having a better arthritis suppressor effect than higher doses of CII in DBA/1 Lac J mice described by Dr. Myers and colleagues, and is in contrast to the direct dose response when APL A12 is given IV to DR1 mice (i.e. arthritis is directly proportioned to dose of APL A12) (See Table I).

FIG. 1 shows groups of 10 DR1 transgenic mice that were fed orally PBS, A12 10 μg, A12 50 μg or A12 100 μg for 8 days over 2 weeks and then immunized with CII. Arthritis severity was scored and recorded. The graph shown in FIG. 1, shows the mean severity score on y-axis 150 and the days after immunization on x-axis 160. Shown are graphs for groups receiving PBS 110, A12 10 ug 130, A12 50 ug 140, and A12 100 ug 120.

TABLE I

Effect of Intravenous A12 on CIA in DR1 Transgenic Mice

| Antigen | Incidence* | Antibodies to CII** |
|---|---|---|
| Ova (1 mg) | 7/10 | 42 ± 10 |
| A12 (0.01 mg) | 5/10 | 33 ± 11 |
| A12 (0.5 mg) | 3/10 | 24 ± 7 (p ≤ 0.025) |
| A12 (1 mg) | 1/10 (p = 0.01) | 22 ± 9 (p ≤ 0.025) |

Groups of DR1 Transgenic mice were immunized intradermally in the tail with 100 μg of CII in complete Freund's adjuvant. A12 was administered intravenously at either 333 μg/dose for a total of 3 doses (1 mg total), 166 μg/dose × 3 (0.5 mg total), or 33 μg/dose × 3 (0.1 mg total) on days 10, 12, and 14 following CII-immunization.

APL A12 Downredulates Th1 Cytokine Production by RA PBMC In Vitro

We assessed the ability of APL A12 added to cultures of PBMC to affect production of IFNγ and other Th1 and Th2 cytokines by the cultured PBMC stimulated with α1(II) from 18 RA patients, 16 of whom had known HLA DR B1 haplotypes. 16 of these patients were taking methothexate, 10 NSAIDS and 12 anti-TNF agents. One patient was taking Arava. Isolated PBMC were resuspended in Dulbecco's minimal essential medium containing penicillin (100 U/ml), streptomycin (100 μg/ml), 9% fetal calf serum (FCS), and non-essential amino acids thereafter referred to as "Complete Medium" at a concentration of $4 \times 10^6$ cells/ml. Aliquots (0.5 ml) of the cell suspension were dispensed into wells of 48 well tissue culture plates (NUNC, Roskilde, Denmark). To designated wells containing the cell suspensions, APL A12 (85% pure synthesized by (Neo MPS, Inc., San Diego, Calif. at final concentrations of 25 μg/ml, 10 μg/ml and 1 μg/ml were added and incubated at 37° C. in a 5% $CO_2$ humidified atmosphere for one hour prior to addition of α1(II) (50 μg/ml). After 48 h, a 50 μl aliquot was removed from each well and frozen at −70° C., and after 144 h of culture, supernatants were harvested and stored at −70° C. until analyzed for levels of Th1/Th2 cytokines by BioRad cytokine multiplex assays. As shown in Table II, APL A12 down-regulated IFNγ production by ≥50% in 7 of 10 patients with the RA susceptibility shared epitope and 2 of 6 patients without the shared epitopes. In preliminary studies, we assessed the effect of APL A12 alone on IFNγ production by RA PBMC, and found no change from PBS control in IFNγ production (data not shown).

These data suggest APL A12 is effective in reducing IFNγ production by RA PBMC stimulated in vitro with α1(II) in RA patients taking DMARDS, NSAIDs and anti-TNF treatment. It is interesting that in some patients not having any of the recognized shared epitope alleles, APL A12 downregulated IFNγ production suggesting APL A12 may be promiscuous and interact with other than "shared epitope" MHC molecules. These patients had the following HLA DR B1 alleles: *0301/01501 and *0701/*1601.

Analysis of 48 h PBMC culture supernatants with a 27 cytokines multiplex assay revealed that other cytokines/chemokines/growth factors in addition to IFNγ are modulated by APL A12. These data are shown in Table III.

At 48 h of culture, there was down regulation by APL A12 of IL-1ra, IL-2, IP-10, PDGF-bb, RANTES and TNFα while IL-10 was upregulated by APL A12 (Table III). These cytokines/chemokines play roles in RA not fully understood. For example, RANTES and IP-10 are increased in RA synovial fluid, wherein RANTES may attract monocytes, lymphocytes, and neutrophils into the joint. IP-10 may play a role in trafficking T cells into inflamed RA joints. PDGF is involved in proliferation of synovial fibroblasts. The Bio Rad 27 multiplex may detect similar changes in these and other cytokine/chemokines/growth factors as a consequence of APL A12 administration to patients with RA.

TABLE II

APL A12 Inhibition of IFNγ Production by RA PBMC*

| | | α1(II) | A1(II) + APL A12 | | |
|---|---|---|---|---|---|
| Patient | HLA/DRB1 | | 25 µg/ml | 10 µg/ml | 1 µg/ml |
| | | | IFNγ Stimulation Index | | |
| | Shared Epitope | | | | |
| 85 | *15/*04 | 75 | −24 | −54 | −65 |
| 86 | *0101/*0404 | 271 | 1 | −66 | −74 |
| 91 | *0101/*0701 | 474 | 15 | 291 | — |
| 93 | *0401/*1303 | 139 | 113 | 68 | 139 |
| 121 | *0101/*0401 | 114 | 123 | 37 | 49 |
| 122 | *0301/*0405 | 317 | 493 | 1220 | 742 |
| 124 | *0102/*0404 | 1230 | 1350 | 644 | 908 |
| 129 | *0101/*1401 | 2510 | 2620 | 2111 | 3190 |
| 131 | *0404/*0701 | 214 | 154 | 93 | 85 |
| 132 | *0401/*0401 | 95 | 83 | 110 | 203 |
| Mean ± SEM | | | | | |
| | No Shared Epitope | | | | |
| 90 | *0301/*1501 | 123 | 16 | 12 | 49 |
| 92 | *0701/*1601 | 99 | 50 | −3 | 45 |
| 123 | *13/*04 | 1590 | 934 | 1220 | 1120 |
| 126 | *0301/*0701 | 707 | 778 | 807 | 928 |
| 128 | *0301/*0701 | 448 | 357 | 479 | 586 |
| 130 | *0301/*0301 | 66 | 106 | 91 | 75 |
| Mean ± SEM | | | | | |
| | HLA Unknown | | | | |
| 88 | | 424 | 121 | 73 | 42 |
| 127 | | 111 | 214 | 180 | 228 |

*Values are an IFNγ Stimulation Index Calculated as follows:

$$\frac{\alpha(II)IFN\gamma - PBS\ IFN\gamma}{PBS\ IFN\gamma} \times 100$$

PBMC were cultured for 1 h with or without APL A12 and then with or without addition of α1(II) 50 µg/mL. After 144 h culture, IFNγ levels were measured in PBMC supernatants by ELISA.

Down Regulation of RA CD4+ T Cells Expressing IFNγ and IL-17 by APL A12

Figure 2:
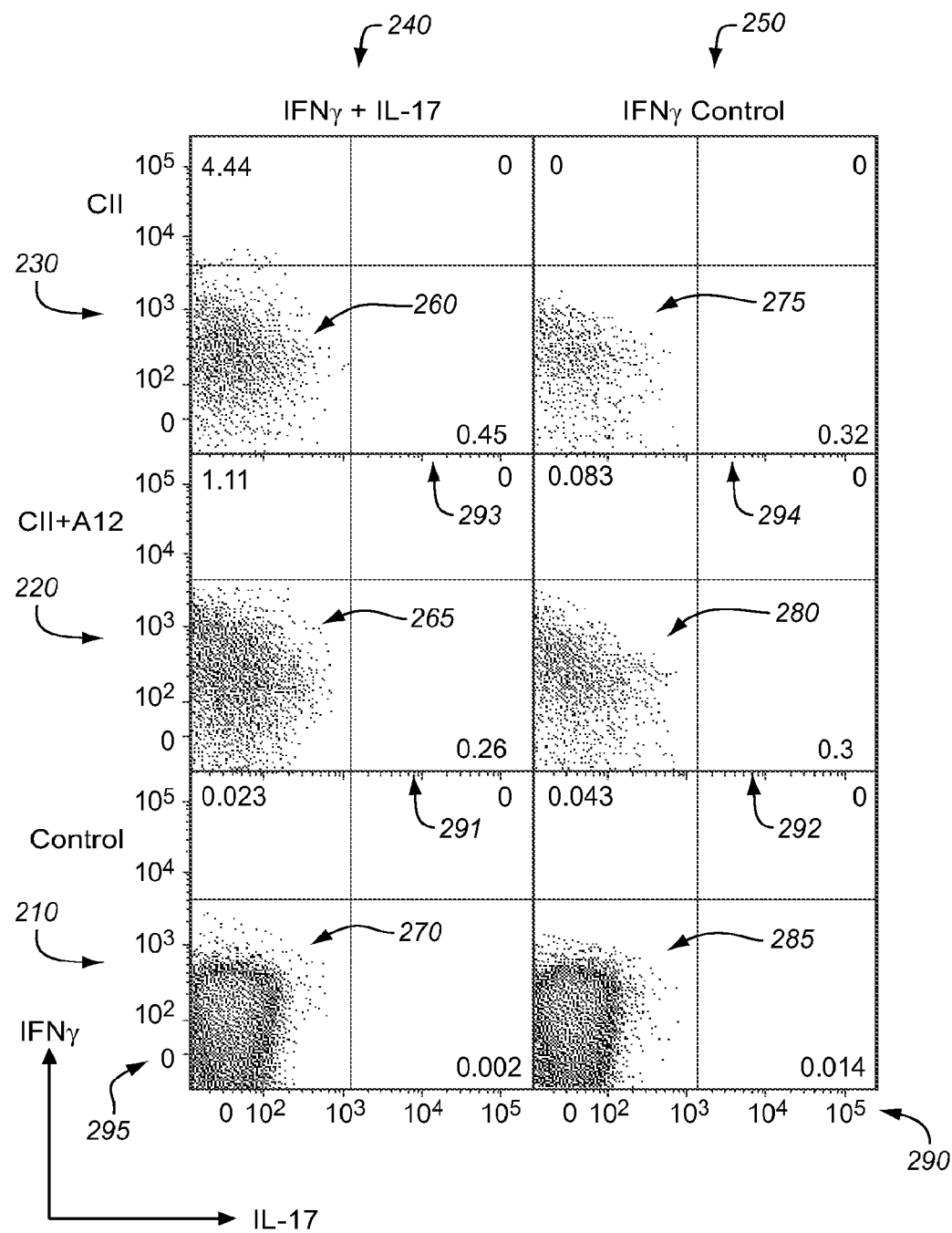
FIG. 2 shows CII and A12 stimulated peripheral blood lymphocyte cultures with intracellular cytokine production.

We assessed the effect of APL A12 added to cultures of RA PBMC stimulated with α1(II) on CD4+ T cells expression of IFNγ and IL-17 as shown in FIG. 2. CII stimulation of PBMC from a RA patient induces the production of IFNγ and IL-17 by CD4+ T cells, and that co-incubation of the A12 analog peptide with the CII resulted in 75% decrease in the number of IFNγ-producing T cells, and a 42% reduction in IL-17 producing T cells (FIG. 2).

As shown in FIG. 2, blood lymphocytes were placed in a culture. The flow use an IFNγ scale on y-axis 295 and IL-17 on x-axis 290, 291, 292, 293, 294 (log scale). The results of the flow are shown for Control 210 including IFNγ+IL-17 flow 270 and IFNγ Control flow 285. The results of the flow are shown for CII+A12 220 including IFNγ+IL-17 flow 265 and IFNγ Control flow 280. The results of the flow are shown for CII 230 including IFNγ+IL-17 flow 260 and IFNγ Control flow 275. Columns 240, 250 represent IFNγ+IL-17 flow and IFNγ Control flow, respectively. Peripheral blood lymphocytes were placed in culture (2×106/well, 24 well plate) and stimulated with either CII alone (50 µg/ml), CII+A12 peptide (10 µg/ml), or PBS for 5 days. During the last 6 hours of culture, cells were stimulated with of PMA and ionomycin (5 ng/ml and 500 ng/ml, respectively), and monensin (0.83 µg/ml, BD Biosciences) was added during this culture period to enhance the detection of intracellular cytokine production. Cells were then collected and analyzed by flow cytometry using fluorochrome-labeled antibodies specific for CD4, CD8, CD69, IL-17 and IFNγ. Staining for intracellular cytokine expression was performed after permeabilization of the cells. Data are based on a minimum of 75,000 events analyzed. The IFNγ Controls (right panels) are based on the fluorescence minus one (FMO) approach whereby the antibody of IFNγ is omitted from these samples to make sure that no fluorochrome was spilling over into the IFNγ detector.

Summary

Experiments with transgenic mice prove that the DR1 and DR4 immune response genes associated with RA are capable of supporting the development of autoimmune responses to CII and of mediating inflammatory arthritis. Both of these mouse strains react to the same immunodominant determinant $CII_{263-270}$. Whether the selection of this determinant is related to the "shared epitope" has not yet been proven, but crystallographic data support the interaction of $CII_{263-270}$ with at least amino acids of this epitope (4). A potential means by which CII autoimmunity can be down-regulated in this animal model using synthetic CII analog peptides has been

TABLE III

Modulation of APL A12 Cytokines/Chemokines/Growth Factors in RA PBMC Cultures

| | IL-1ra pg/mL | IL-2 pg/mL | IL-10 pg/mL | IP-10 pg/mL | PDGF-bb pg/mL | RANTES pg/mL | TNFα pg/mL |
|---|---|---|---|---|---|---|---|
| PBS | 1738 ± 433 | 7 ± 1.3 | 323 ± 104 | 115 ± 64 | 169 ± 53 | 1612 ± 529 | 229 ± 74 |
| α1(II) | 3893 ± 520 | 59 ± 42 | 191 ± 63 | 1466 ± 528 | 595 ± 190 | 4607 ± 2977 | 1693 ± 925 |
| α1(II) + APL A12 | 2013 ± 220 | 6 ± 0.9 | 555 ± 104 | 114 ± 91 | 39 ± 25 | 750 ± 183 | 84 ± 17 |
| P value 1* | 0.010 | 0.002 | 0.24 | 0.004 | 0.132 | 0.485 | 0.818 |
| P value 2** | 0.004 | 0.002 | 0.026 | 0.004 | 0.009 | 0.026 | 0.041 |

*Comparison of PBS with α1(II) using Mann-Whitney rank sum test
**Comparison of α1(II) with α1(II) APL A12 using Mann-Whitney rank sum test
† PBMC from 6 RA patients were cultured for 48 h with PBS, α1(II) 50 µg/ml, or APL A12 10 µg/ml + α1(II) 50 µg/ml in Complete Medium. Previous assay showed these patients PBMC stimulated with α1(II) produced increased IFNγ and this was inhibited by APL A12. Supernatants were analyzed by Bio Rad 27 human cytokine multiplex assays. Other cytokines/chemokines/growth factors including IL-1β, IL-4, IL-5, IL-6, IL-7, IL-8, IL-9, IL-12 p70, IL-13, IL-15, IL-17, Eotoxin, bFGF, G-CSF, GM-CSF, MCP-1, MIP-1α, MIP-1β and VEGF were not modulated at 48 h of culture.

identified. One of these peptides, A12 has been shown to be an effective inhibitor of CIA in both DR1 and DR4 transgenic mice. This disclosure provides an evaluation of A12 in RA patients to determine its potential to regulate the immune response to CII in patients with RA, and gain some insight into its mechanism of action and clinical effects in RA. In addition, this disclosure also contemplates addition of one or more simple or complex carbohydrates to the A12. Such one or more carbohydrates may enhance the potency of the APL A12.

Determination of Doses of APL A12 that Decrease Immune Reactivity to CII in Patients with RA Dose response data using DR1 transgenic mice showed that low (50 and 10 μg/day) rather than higher dose (100 μg) of APL A12 protected mice against arthritis induced by CII immunization. This suggests that a low-dose of APL A12 might be more effective at down regulating CII immunity in patients with RA than a high dose. We plan to test three doses of APL A12 from 30 μg/day to 1,000 μg/day. We believe we will increase the chances of seeing a statistically significant effect of oral APL A12 in down regulating CII immunity if we enroll only RA patients who have a demonstrated in vitro suppression of IFNγ production by α1(II)-stimulated PBMC in the presence of APL A12.

Experimental Approach

The study will have 4 treatment arms each with 10 patients who have demonstrated T cell immunity to CII and have an in vitro response to APL A12 at the screening visit. Patients will be randomized to one of the 4 treatment arms. Each of the 4 treatments will be given for 16 weeks.

In keeping with a sequential dose escalation strategy, the originally proposed randomization scheme will be modified so that subjects will be randomized to receive either the lowest dose (30 μg) or placebo (Block 1), followed by the next higher dose (300 μg) or placebo (Block 2), and finally followed by the highest dose (1000 μg) or placebo (Block 3). We will begin with the lowest dose (30 μg/day) and enroll 6 to receive 30 μg/day APL A12 and 2 to receive placebo for 16 weeks. Results will be reported to the DMC for a decision to proceed to the next block based on indications of safety. If this dose does not cause adverse events or toxicity or worsens RA, we will proceed to enroll 6 patients to receive 300 μg/day APL A12 and 2 to receive placebo for 16 weeks. Results will be reported to the VA Data Monitoring Committee (DMC) for a decision to proceed to the next block based on indications of safety. If this dose does not cause adverse events or toxicity or worsens RA, we will proceed to enroll 6 patients to receive 1000 μg/day APL A12 and 2 to receive placebo for 16 weeks. Results will be reported to the DMC for a decision to proceed to the next block based on indications of safety.

| Block | Active Drug Dose | Number of Treated Subjects | Number of Placebo Subjects |
|---|---|---|---|
| 1 | 30 | 6 | 2 |
| 2 | 300 | 6 | 2 |
| 3 | 1000 | 6 | 2 |
| 4 | 30 | 4 | 6 |
|   | 300 | 4 |   |
|   | 1000 | 4 |   |

Interim analyses will be conducted after the first three blocks are completed to determine whether there is a trend toward reduction of net IFNγ concentration in α1(II)-stimulated PBMC culture supernatants. After each of the 3 blocks, interim analysis will be conducted to assess safety (i.e. adverse events, toxicity, or arthritis worsening). Note that the sequential dose escalation strategy with successive interim analyses conducted prior to moving to the next dose will reveal the treatment assignments to the study statistician, regardless of the coding of the actual assignments. Thus, the study statistician will be an unblinded statistician.

If, after completion of the third block and interim analysis for reduction in net IFNγ concentration in α1(II)-stimulated PBMC culture supernatants, all doses appear to be safe and at least one dose is associated with an indication of efficacy, permission will be requested from the DMC to proceed to the final block (Block 4) and complete the randomization process with all of the remaining 18 subjects.

If, after completion of the third block, the proposed doses appear to be safe, but none appears to be efficacious, then alternative dosing strategies will be proposed as discussed elsewhere. (See Potential Problems and Alternative Approaches)

Because we are leaving RA patients enrolled in the study on DMARDs, anti-TNFα biologics, low dose prednisone and NSAIDs, we will stratify patients to treatment groups based on types of medications they are taking. We will enroll patients with a disease activity score (DAS 28) of ≤3.2. DAS 28 will be measured as previously described. PBMC will be set up in culture with and without α1(II) at screening visit to assess levels of net IFNγ concentration in α1(II)-stimulated PMBC culture supernatants and with A12+α1(II) to assess whether patients with increased IFNγ production by stimulation of their PBMC with α1(II) have reduction in net IFNγ when A12 is added to α1(II)-stimulated PBMC cultures. IFNγ production will be used as an indicator of T cell immunity to CII since it is produced in greater quantities than IL-2 or IL-17. RA patient PBMC generally proliferate poorly or not at all to α1(II) native CII or α1(II) CB peptides (11, 74). In the NIH oral CII study, we found that 60% of RA patients produce increased IFNγ when their PBMC are cultured with α1(II) and 50% responded to APL A12 in vitro. Therefore, we will need to screen approximately 160 patients to identify 42 that have increased net IFNγ concentration in α1(II)-stimulated PBMC cultures compared to unstimulated PBMC cultures and have 50% reduction in net IFNγ concentrations in APL A12+α1(II) cultures compared to α1(II) stimulated PBMC cultures.

For Specific Objective 1, PBMC will be set up with α1(II) for patients randomized to enter the study at baseline, and weeks 8 and 16 to assess IFNγ production by α1(II)-stimulated PBMC. For Specific Objective 1b, we will assess levels of other Th1, Th2 and Th3 cytokines in PBMC cultured with α1(II), APL A12, anti-CD4/CD28 microbeads and PBS at baseline and weeks 8 and 16. For Specific Objective 1c, cell layers of PBMC cultures from screened patients will be saved for HLA typing. For Specific Objective 2a and b PBMC will be analyzed at baseline and 8 and 16 weeks. For Objective 2a, functional suppression will be assessed at baseline and at 8 and 16 weeks. For Objective 2b, intracellular cytokines will be assessed by flow cytometry at baseline and at 8 and 16 weeks.

Primary Outcome Variable:

The primary outcome variable will be a significant reduction from baseline values of net IFNγ concentration in supernatants of α1(II)-stimulated PBMC cultures after 16 weeks in patients receiving APL A12 compared to placebo.

Secondary Outcome Variables:

Number of swollen and tender joints, ESR, CRP, rheumatoid factor, antibodies to CII, MHAQ, Patients' Global Assessment, and Physicians' Global Assessment will be secondary outcome variables as well as reduction in DAS 28.

Since we expect APL A12 to suppress CII immunity equally in men and women and all races and also to maintain statistical power, subpopulations will not be analyzed or specifically recruited. All races will be recruited for this.

Safety Monitoring:

Patients will be assessed for presence of adverse events. An Adverse Experience (AE) is any unfavorable and unintended change in the structure, function or chemistry of the body manifested as signs, symptoms, or laboratory test abnormalities considered or not considered related to the use of APL A12. Pre-existing conditions are not AE's. Any worsening of a pre-existing condition is an AE. Procedures are not AE's. The reason for a procedure is an AE. Adverse events will be reported two times monthly as required by our IRB, annually to the FDA and every six months to the DMC [except serious adverse events (SAEs)]. Adverse experiences are rated as follows: 1) Mild: the patient has enough awareness of sign or symptom, but it is easily tolerated. 2) Moderate: The adverse experience causes enough discomfort so as to interfere with normal activity. 3) Severe: The adverse experience is incapacitating, i.e., the patient is unable to work or engage in usual activities or has to be admitted to the hospital for treatment. Since this is an immunotherapy, we will be vigilant for the occurrence of other autoimmune disease manifestation (e.g. muscle weakness, paralysis, paresthesias, skin rash, mental or behavioral changes, etc.).

Stopping Criteria that Preclude Continued Treatment of Patients Experiencing a Significant Disease Flare:

Since there could be a paradoxic increase in RA disease activity, we will discontinue administration of study medication to patients in the study that have increase in DAS 28 to 5.1 (high disease activity) and/or those who have any incremental increase of >1.2 units in the DAS 28. If patients develop hypersensitivity reactions (hives, itching, wheezing, syncope), or develop manifestations of other autoimmune diseases, they will be dropped from the study and the DMC, IRB, and FDA will be notified. The DMC will advise Dr. Postlethwaite whether to put a hold in the study.

Potential Problems and Alternative Approaches:

We will have to screen approximately 160 patients with RA with a DAS≤3.2 to identify 70 patients with CII immunity and 42 who respond in vitro to APL A12. Since oral tolerance is short-lived, patients off CII for one year or more will be eligible to participate in the protocol. We will equally randomize patients who were treated with oral CII in the study in FIG. 1 into each of the treatment arms.

If it turns out that none of the 3 doses of APL A12 is working (i.e. causing ≥50% reduction in IFNγ from baseline), we will adjust the doses of APL A12. We will have one dose of 150 µg/day, one of 650 µg/day and one of 2,000 µg/day. We will essentially start the study over with plans to screen enough patients to enroll 42 different RA patients.

There is a chance that APL A12 may exacerbate RA. Disease exacerbation occurred in one study of one APL of myelin basic protein (MBP) in a Phase II trial in patients with multiple sclerosis (MS). The MBP APL, CGP77116 was given at doses of 5-50 mg subcutaneously once a week for varying periods of time. In contrast to our study, there was no pre-screening of patients' PBMC to determine whether MBP APL upregulated or down regulated Th1 response to MBP. There was induction of IL-5 by the MBP APL. A different MBP APL (NBI 5788) did not induce disease exacerbation or improvement but had a 9% hypersensitivity reaction rate to the subcutaneous injection of 50 mg/week of MBP APL. Our study differs considerably from both of these MS studies in that the CII APL A12 will be administered orally rather than via the subcutaneous route. This may lessen the chance of hypersensitivity reactions and the dose is 10-100× less than the doses used in the two MS studies described above. Nonetheless, we will carefully monitor patients for evidence of disease exacerbation by following the ACR responses and DAS 28 response parameters and will stop study drug if the above criteria for increased DAS is observed. We will inform patients to contact us if there is the appearance of hives, angiodema, difficulty breathing or other skin rash or unusual symptoms in addition to a flare of RA symptoms. We will see all patients one week and 4 weeks after starting treatment to carefully assess development of other adverse events. In contrast to the MS experience, an insulin APL study did not show hypersensitivity or exacerbation of diabetes, nor did the orally administered HSP APL in a RA study.

Determining APL A12 Modulation of Th1/Th2/Th3 Cytokine Profiles in α1(II)-Stimulated PBMC Cultures Our preliminary data using addition of APL A12 to α1(II)-stimulated RA PBMC cultures showed that APL A12 caused a down regulation of Th1 cytokines IFNγ, TNFα and IL-2 and an up regulation of the Th2 cytokine IL-10 in the culture supernatants (Table II and III). Interferon induced protein (IP-10) was also decreased as were PDGF-bb, IL-1ra, and RANTES. In order to learn more about the extent and variety of cytokines/chemokines/growth factors that might be modulated by in vivo administration of APL to RA patients, we believe it will be important to perform an in-depth assessment of an array of cytokines, chemokines/growth factors by employing BioRads 27 human cytokine multiplex assay. This 27 multiplex assay includes all Th1 and Th2 cytokine and several chemokines/growth factors involved in RA pathogenesis. We believe this discovery approach is justified in a Phase I study in which we are trying to learn as much as possible about the impact of APL A12 on immune and inflammatory parameters in patients with RA. The results could generate new hypotheses to test as to the mechanisms of action of APL A12. We will also assess cytokine/chemokine/growth factor production using the 27 multiplex assay in PBMC cultured with APL A12 alone. Studies treating type I diabetics with NBI-6024, an APL of insulin $B_{9-23}$ epitope, showed that in in vitro cultures, NBI-6024 upregulated Th1 cytokines in T cells from the placebo treated patients, but upregulated IL-4, IL-10 and IL-5 in T cells from NBI-6024 treated patients.

Experimental Approach:

The primary cytokine readout for altered immune response in Specific Objective 1a is a significant reduction (≥50%) at 8 or 16 weeks in IFNγ concentration in supernatants from α1(II)-stimulated PBMC cultures in one more of the APL A12 treatment groups compared to placebo treated patients. In this objective, we will assess levels of other Th1/Th2/Th3 cytokines in the same culture supernatants and in supernatants from APL A12-stimulated cultures to better characterize the changes in cytokine profiles induced by APL A12 treatment. Other chemokines/cytokines/growth factors known to be involved in RA pathogenesis will be assessed using BioRad 27 human cytokine multiplex assay which is in routine use at the VAMC.

Culture of PBMC for Th1/Th2/Th3 Cytokines:

PBMC will be isolated from EGTA anti-coagulated blood as in Specific Objective 1 above at week 0 (Pre-treatment), and weeks 8 and 16. The PBMC will be suspended at a concentration of $4 \times 10^6$ cells/mL Complete Medium. Aliquots (450 µl) will be dispensed into wells of 48 well NUNC tissue culture plates. To 2 wells each, the following will be added: 25 ug (in 50 ul PBS) bovine α1(II), and APL A12 5 ug in 50 ml PBS, PBS is an unstimulated control and 5 uL Dynal anti-CD3/CD28 microbeads. Because serum contains TFG-β1 and TGF-β2 and perhaps TGF-β3, for the Th3 cytokines, TGF-β1, TGF-β2 and TGF-β3, the PBMC will be cultured as above except in serum-free EXVIVO (GIBCO) medium containing penicillin 100 U/uL and streptomycin 100 µg/mL. Cell cultures will be placed in a 37° C. tissue culture incubator containing a humidified atmosphere and 5% $CO_2$. Supernatants from the PBMC cultures in complete medium will be harvested after 48 hours and after 144 hours of culture. Supernatants will be harvested from the EXVIVO cultures after 48 hours for TGFβ ELISAs.

Potential Problems and Alternative Approaches:

We would anticipate that if the correct dose of APL A12 is administered to RA patients that in prescreening had a reduction in IFNγ production by PBMC cultured with APL A12+ α1(II), there will be down regulation of several Th1 and upregulation of several Th2/Th3 cytokines. Furthermore, the multiplex assay is very sensitive and should be able to detect changes in cytokines/chemokines/growth factors. The Molecular Core has considerable technical expertise and problems are not anticipated. We have considered limited dilation analysis to detect changes in numbers of Th1 and Th2/Th3 producing T cells. Unfortunately, since human T cells do not proliferate well in response to CII, limited dilution assay would be difficult or impossible. Prolonged culture with IL-2 or IL-7 may also change cytokine profiles.

Determining if In Vitro APL A12 Down Regulation of IFNγ Production by α1(II)-Stimulated RA PBMC is Related to HLA DRB1 RA Shared Epitope Alleles APL A12 was patterned after the amino acid sequence in CII that binds to HLA DRB1*0101 MHC. Other DRB1 shared epitope alleles (or as our preliminary data suggest non-shared epitope alleles) might interact with APL A12 and down regulate IFNγ production by T cells. It will be important to know which HLA DRB1 alleles are or are not present in RA patients being screened that have in vitro IFNγ production suppression being screened to APL A12. These results may allow us to identify which DRB1 alleles are necessary for an APL A12 response to occur.

Experimental Approach:

The cell layers from PBMC cultures from all patients screened in Objective 1a above will be harvested and frozen at −70 until HLA DRB1, DQA1 and DQB1 typing is done. IFNγ levels will be measured in 144 h PBMC culture supernatants described in Objective 1a. HLA typing will be done on a fee per sample basis by University of Tennessee Tissue Typing Laboratory on the patients who have IFNγ down-regulation of APL A12+α1(II)-stimulated PBMC cultures. An α1(II) IFNγ level ≥100% of the PBS IFNγ value will define α1(II) responders. HC Peptide 1 (APL A12) responders in vitro will be defined as ≥50% reduction in IFNγ concentration in PBMC culture with APL A12 added to α1(II) cultures from the IFNγ concentration in PBMC cultured with α1(II) alone.

The % change in IFNγ α1(II) for APL A12+α1(II) culture from net IFNγ concentration for α1(II) culture will be calculated as follows:

$$\frac{[\alpha 1(II)IFN\gamma] - [APLA12 + \alpha 1(II)IFN\gamma]}{\alpha 1(II)IFN\gamma} \times 100$$

Potential Problems and Alternative Approaches:

Approximately 70% of the patients screened should have one or more of the RA shared epitope alleles. If the trend we saw in the small preliminary data sample holds true for the larger sample size, the majority of APL A12 responders will have one or more of the shared epitopes. We do not anticipate any technical problems with the approach we have outlined since the techniques are in routine use in our laboratory. Each month we will prepare a fresh stock solution of APL A12 dissolved in PBS, filter sterilized and stored at 4° C. APL A12 stored at 4° C. in solution retains it biologic activity for >30 days. A fresh solution of α1(II) will also be prepared each month and stored at 4° C. and handled using sterile technique.

Determining Doses of APL A12 Administered to RA Patients to Generate Functional T Regulatory Cells $CD4^+$ $CD25^+$ FoxP3 T regs have been characterized as defective in patients with RA in that they may suppress the proliferation of autologous $CD4^+$ $CD25^-$ T cells but do not suppress production of IFNγ and other Th1 cytokines. An intriguing question is whether APL A12 will increase the suppressive function of $CD4^+$ $CD25^+$ T regs after 8 and 16 weeks treatment such that their ability to suppress IFNγ production by autologous α1(II) stimulated PBMC (isolated and cryopreserved at baseline) will be increased.

Experimental Approach:

PBMC EGTA anti-coagulated from 15 ml blood will be isolated from each patient at baseline and cryopreserved according to a strict protocol (74). PBMC will be washed and prepared for cryopreservation by aliquoting $5 \times 10^6$ cells in 1 ml ice-cold FBS and by gentle addition of 1 ml ice-cold DMSO (20% in RPMI 1640 medium) into precooled plastic vials fitted with a screw top and rubber O ring. Cells will be placed on ice for 5 minutes and then placed in an eryo 1° C. Freezing Container (Nalgene Catalog No. 5100-0001) which will be placed in a −80° C. freezer overnight and then stored in a liquid nitrogen container (74). These cryopreserved PBMC will be thawed when ready to use by placing each frozen vial into a 37° C. water bath, placed on ice and washed ×1 in complete medium.

At baseline (cells will have been frozen for 4 h) and at 8 and 16 weeks, PBMCs will be recovered from cryopreservation and used in assays to measure T reg function. $CD4^+$ $CD25^{+hi}$ T regs have been shown to uniformly express FoxP3 and will be prepared from a $CD4^+$ T cell population from freshly obtained PBMC (20 ml heparinized blood) by negative selection using the AutoMACS (Miltenyi Biotec). The enriched T cells will be stained with anti-CD4– cychrome and PE-conjugated anti-CD25 (10 µg/$10^7$ cells) for 20 minutes at 4° C. CD4+ and $CD25^{hi}$ T regs will be purified using a MoFlo high speed cell sorter (Dako Cyotmation) to a purity of 98%. An aliquot, $10^5$ cells, will be stained for FoxP3 which will be expected to be 100% $CD4^+$ $CD25^{hi}$ T cells.

Figure 3A:
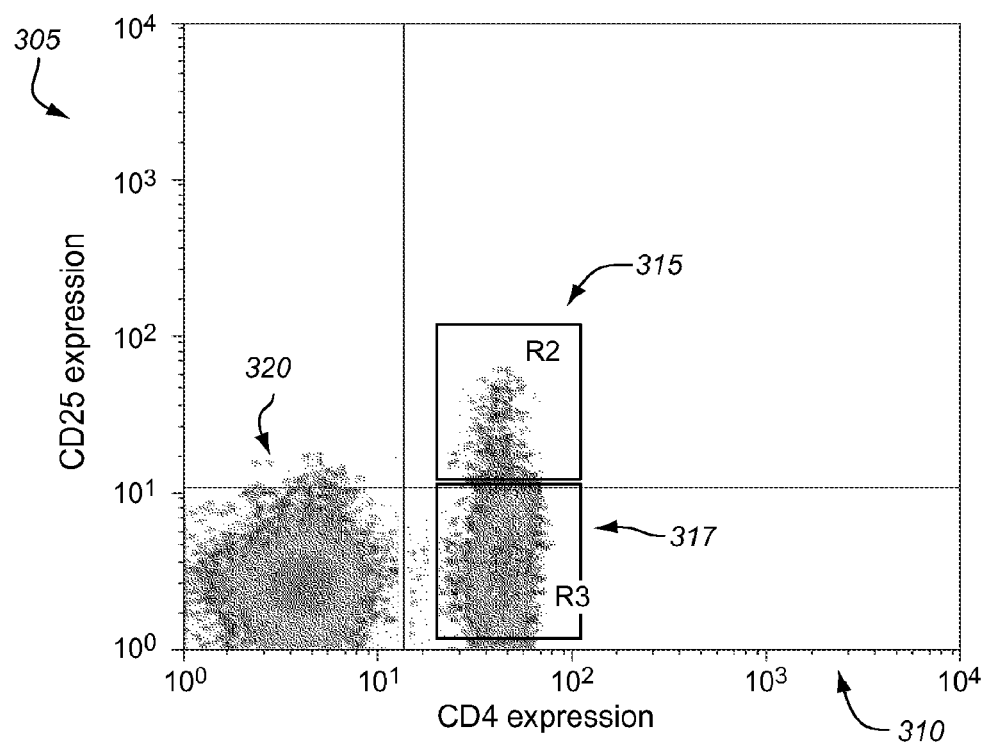
FIGS. 3A and 3B show representative flow cytometry analysis of FoxP3 staining of normal human PBMC.
Figure 3B:
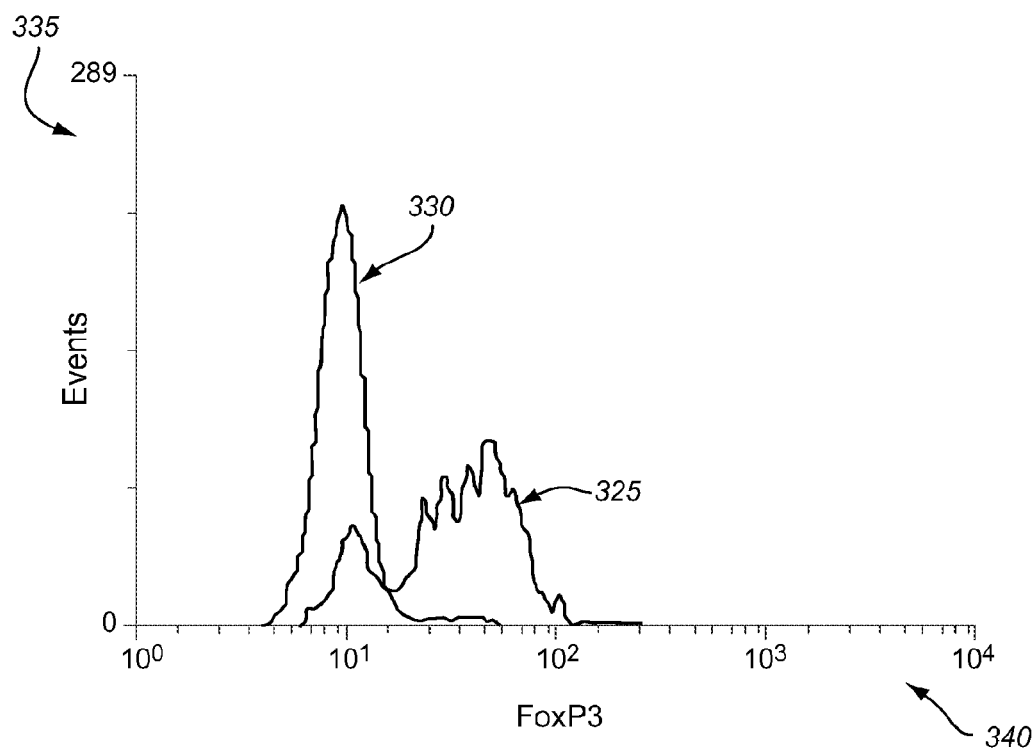

Cells will be washed in cold PBS and resuspended in 1 ml of freshly prepared Fix/Perm Buffer per sample. FITC anti-FoxP3 MOAB will be added and cells will then incubated at 4° C. for 1 hour in the dark and subsequently will be washed with PBS (×1) and Permeabilization Buffer (×2). Non-specific binding will be reduced by blocking with 2% (2 µL) normal rat serum in 1× Permeabilization Buffer, in approximately 100 µL volume, at 4° C. for 30 minutes in the dark. After washing twice with Permeabilization Buffer, cells will be resuspended in Staining Buffer (2% FBS in PBS) and analyzed on the flow cytometer. All Samples will be analyzed by multi-color flow cytometry on a FAC Scan flow cytometer (Becton Dickinson), and the frequencies of T-cell $FoxP3^+$ Tregs will be calculated using FlowJo software (TreeStar Inc, Ashland, Oreg.). FIG. 3A-B. FoxP3 and IL-10 positive cells will be expressed as a percentage of $CD4^+$ $CD25^+$ T cells from a lymphocyte gate.

FIGS. 3A and 3B show representative flow cytometry analysis of FoxP3 staining of normal human PBMC. The left panel, FIG. 3A shows double positive CD4+CD25+ T cells 317 and CD4+CD25− T cells 320, 315. The scale 305 is CD25 expression and the scale 310 is CD4 expression. The scale of FIG. 3B is Events on axis 335 and FoxP3 on axis 340. Two sets of results are shown CD4+CD25− T Cells 330 and CD4+ CD25+ T Cells 325. Gating on this subset demonstrates positive FoxP3 staining in the right panel whereas the CD25− subset are negative for FoxP3.

Suppression Assay:

The thawed PBMC from baseline will be added to 15 wells of round bottom 96 well tissue culture plates (NUNC) $10^5$ PBMC/well. $10^5$ CD4$^+$ CD25$^{hi}$ T cells per well in complete medium at a final volume of 200 µl will be added to six wells containing the PBMC. To three wells containing CD4+ CD25$^{hi}$ T cells+PBMC, α1(II) will be added. Culture will be continued for six days after which time supernatants will be harvested and IFNγ quantitated by ELISA (R & D Systems). The three remaining wells containing only PBMC will have α1(II) added, and three wells with PBMC will have PBS added.

Potential Problems and Alternative Approaches:

The techniques for freezing PBMC are standard and we do not anticipate problems reproducing the viability of the PBMC that are routinely obtained (>90%). We will practice the cryopreservation on RA PBMC until we achieve >90% viability by typan blue exclusion. We considered using CD4$^+$ CD25$^−$ and APC for indicator cells recovered from the auto MACs as bi-products rather than cryopreserved PBMC. However, we are concerned that this population may have been altered by APL A12 treatment. We have stained several normal donor PBMC to master this FoxP3 technique (see representative in FIG. 6). We will titrate the amount of antibody required to reduce background staining, and we will perform preliminary experiments for set-up of the cytometer and compensation settings. All patient samples will be analyzed with the same gating and quadrant settings using FlowJo software. In this Specific Aim we will make use of the facilities and expertise of the Flow Cytometry Core at the Memphis VAMC.

Figure 6:
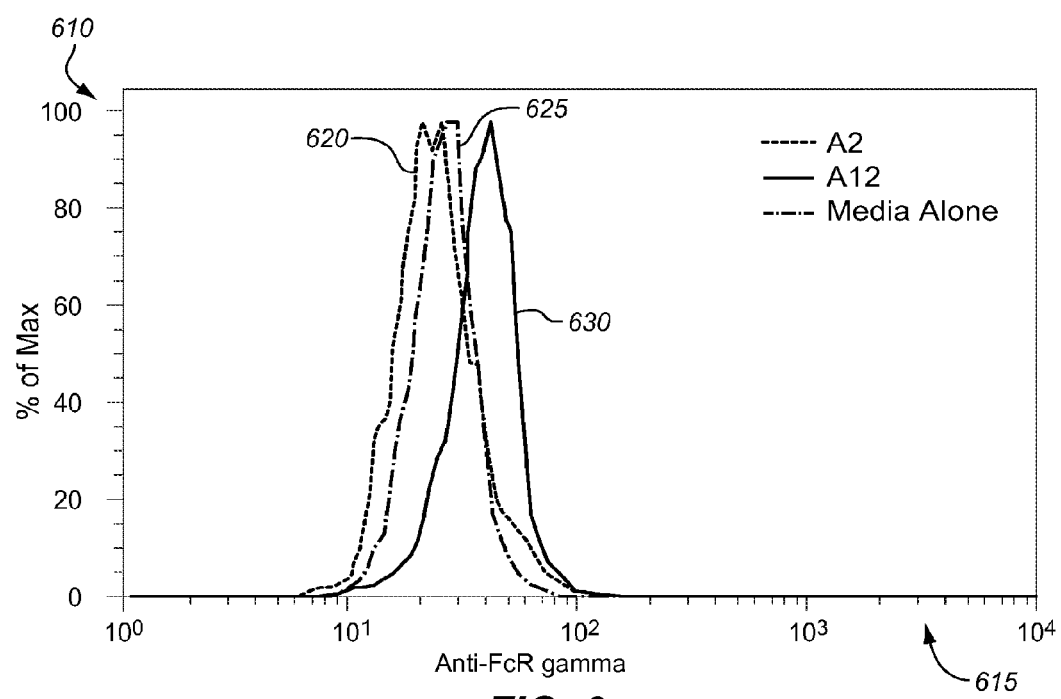
FIG. 6 shows A12 influenced expression in Splenocytes.

In FIG. 6 it is shown that A12 treatment increases FcεRIπ expression. In the graph with axis 610 for the percentage of the maximum, axis 615 for the number of occurrences on a log scale, line 620 is for A2, line 625 is for media alone, and line 630 is for A12. Splenocytes from DR1 TCR transgenic mice were cultured for 48 hours in the presence of A12 (dark grey line), A2 (black line) or media alone (light grey line). Using an antibody specific for the FcR gamma chain and specific gating on CD4+ cells, we demonstrate that T cells activated by A12 significantly upregulate the expression of FcεRIπ, indicating a unique A12-activated phenotype. The cells cultured with A2 peptide are no different than unstimulated controls.

Determining the Cytokine Profile in T Cells in RA Patients Who are Treated with APL A12 Compared to Placebo Our preliminary data show that APL A12 in DR transgenic mice immunized with CII induces a shift in Th1 to Th2 cytokine (see Background Section). We believe it will be important to search for changes in α1(II)-specific T cell cytokine profile from Th1 to Th2. We will determine surface phenotype and intracellular IL-2, IFNγ, IL-17, IL-4, IL-5 and IL-10. Assessment of intracellular levels of these cytokines was demonstrated in an APL of heat shock protein in the adjuvant arthritis rat model. Nasal administration of heat-shock protein 60 180-188 T cell epitope alanine 183, induced down regulation of IFNγ, IL-2 and upregulated IL-4 and IL-10 in CD4$^+$ T cells analyzed by flow cytometry. We chose short term α1(II)- and APL A12-stimulated PBMC culture over generation of short term T cell lines for several reasons. The whole PBMC culture closely mimics the in vivo situation close to the time the PBMC were isolated from the patient. While short T cell lines or cloned T cells from these lines results in larger numbers of a specific type of T cell, the exposure to IL-2 or IL-7 during the expansion phase of developing T cell lines may skew the cytokines towards a TH1 secretion phenotype. Other orally administered antigens in murine models generate a Tr1 IL-10 producing regulatory CD4$^+$ T cell. Tr1 cells were reported to be markedly upregulated in humans tolerized by subcutaneous injection of allergen peptides. APL A12 could induce increased numbers of Tr1 cells. Therefore, we believe it is important to determine whether Tr1 cells (CD4$^+$/IL-10$^+$) are increased by APL A12 treatment.

Experimental Approach:

Peripheral blood mononuclear cells (PBMC) will be isolated from EGTA anti-coagulated venous blood as described in Objective 1a. A single lot of pre-tested FCS will be used throughout the study in the culture/medium, "Complete Medium".

At baseline, 8 and 16 weeks, PBMC will be cultured ($2\times10^6$/ml in each well) in Complete Medium (defined above) with PBS (negative control), α1(II) 50 ug/ml, APL A12 (10 µg/10 ml) alone, α1(II) 50 µg/ml+APL A12 10 µg/ml and Dynal CD3/CD28 microbeads (as a + control). Using flow cytometric methods to detect cytokine production, we will identify functionally distinct T cell subsets in RA PBMCs stimulated in culture with either α1(II), α1(II)+A12 peptide, A12 peptide alone or PBS. PBMCs will be isolated from RA patient blood samples using standard Hypaque protocols. PBMC will be cultured at $2\times10^6$/well 24 well plates in 500 µl of DMEM supplemented with 9% FCS. Our initial experiments will be designed to establish the optimal culture duration for detection of cytokine expression by the T cells as well as its regulation by the A12 peptide. Our analyses will focus on cytokines that are known to be associated with Th1 (IL-2, IL-5, IFN-g), Th2 (IL-4 and IL-10), and Th17 (IL-17) subsets. Because our initial observations have suggested that the mechanism by which A12 acts is likely through a reduction in the production of IFN-γ, we will focus our data analysis on this cytokine in our initial studies, and correlate these data with the presence or absence of the other cytokines. During the last 6 hours of culture, PMA (5 ng/ml), ionomycin (500 ng/ml) and monensin (BD Biosciences) will be added. The addition of PMA and ionomycin will enhance both transcription and translation of the proteins that the cell is currently producing. The addition of monensin will block the secretion of the cytokines, thereby increasing the relative concentration of each inside the cell. The additive effect of these manipulations enhances the sensitivity of the flow cytometry in detecting the T cells producing the cytokines of interest.

Six hours following the addition of PMA, ionomycin and monensin to the PBMC cultures, cells will be washed in PBS and stained with antibodies that bind to surface antigens CD4 and CD8, activation markers CD69, CD71, CD62L and CD25, and CD44 memory markers. After a 30 minute incubation at 4° C., the cells will be washed, and PBMCs will be fixed and permeabilized according to the manufacturer's instruction (Cytofix/Cytoperm, BD Biosciences). Following washes with the perm/wash reagent, fluorochrome labeled antibodies specific for the cytokines of interest will be added, allowed to bind to the cytokines for 30 minutes at 4° C., washed, and analyzed using an LSR II flow cytometer. In our preliminary studies, we have successfully performed seven color flow cytometry, simultaneously detecting three different cytokines and four different cell surface molecules. Although our LSRII cytometer is currently configured to detect up to 13 colors simultaneously, the commercial availability of a wide range of colors for cytokine antibodies is a limiting factor. We have been very successful in performing our own labeling of purified antibody preparations with a wide range of Alexafluor and Qdot dyes, and we will use this approach to expand our detection capabilities. However, because we have chosen to measure intracellular IFN-γ, IL-10, IL-4, IL-2, IL-10, IL-17 and IL-5, it will be necessary to divide these analyses between at least two samples of cells from each culture in order to perform these analyses. In order to obtain statistically significant populations of cytokine producing cells, we will collect a minimum of $5 \times 10^5$ events, and will use the statistical features built-into FloJo software (TreeStar) to analyze our cytometric data.

Potential Problems and Alternative Approaches:

There may be some non-viable cells in 6 day PBMC cultures. These will be removed using a "Dead Cell Removal Kit" from Miltenyi Biotec (Auburn, Calif.). We will also set up additional RA PBMC cultures with α1(II)+ APL A12 and anti-CD4+/CD28+ beads and harvest cells at earlier time points (24, 48, 96 h) to compare staining profile with six day cultures. If earlier time points are found to give better staining and more viable cells, we will adjust the protocol accordingly. Dr. Rosloniec runs the flow cytometry center at the Memphis VAMC and will assist in flow analysis and interpreting flow data.

In the event that we are unable to detect differences in intracellular cytokine staining of T cells, we will switch after the first 8 patients have been studied to use the ELISPOT assay system which is more sensitive than intracellular cytokine detection using the flow cytometry. We will purchase BD ELISPOT reagent sets which will contain capture antibody, detection antibody and SAV-HRP for 10 plates of assays and include 10 uncoated BD ELISPOT plates (BD Biosciences Pharmigen, San Diego, Calif.). We will purchase reagent sets for human IFNγ, IL-17, IL-2, IL-4, IL-5, and IL-10.

For the ELISPOT assay, we will add to each well in a volume of 200 μl, $3 \times 10^5$ PBMC previously isolated by Ficol-Hypaque as in Objective 1a above. The 96 well BD ELISPOT plate will have been coated with either captive antibody for IFNγ, IL-2, IL-4, IL-5, IL-10, or IL-17. Cells will be cultured in triplicate in the presence or absence of 5 μg/ml Tetanus toxoid (Accurate Chemicals, Weldbury, N.Y.) 5 μl anti-CD3/anti CD28-coated microbeads (Dyual), α1(II) 50 μg/ml, and APL A12 10 μg/ml. After 48 h incubation at 37° C. in 5% CO2 humidified atmosphere, cells will be washed away and cytokine detected with the matched biotinylated anti-human IFNγ, IL-2, IL-4, IL-5, IL-17, or IL-10 MOAB. Avidin-HRP conjugate will be added and color developed-with substrate solution (3-amino-9-ethyl carbazole). After color develops the reaction will be stopped by washing the plates with water. Spots derived from cytokine-producing cells will be quantified using the Series-1 Immunospot and Satellite Analyzers (Autoimmune Diagnostics, Inc., Strasberg, Germany).

For statistical analysis of ELISPOT response, we will calculate the stimulation index (SI)=mean antigen-induced spots/mean medium spots for each sample at baseline, 8 weeks and 16 weeks for each patient sample. A change from baseline SI will be calculated for each subject and used as its dependent variable in a Mixed Effects Repeated Measures Model. This will include each treatment group, study weeks of a study group by week interaction as fixed effects in the model with baseline IFNγ concentration used as a covariate. From the model, p-values will be calculated using the Least Squares Means pair-wise difference between each APL A12 dose groups versus placebo at each study week (0, 8 and 16 weeks). A responder analysis will also be conducted where each antigen and cytokine and response rates will be analyzed using Fisher's exact test comparing separately each APL A12 dose group versus placebo group.

Statistical Analysis

Data Analysis and Interpretation:

We want to determine whether one or more doses of APL A12 is superior to placebo in reducing the net α1(II) IFNγ≥50% from baseline after 16 weeks of treatment. Because of the sequential dose escalation strategy, each dose group will be compared separately with the placebo group, as described below.

Analysis of the Primary Outcome Variable.

The primary outcome variable is the presence or absence of a ≥50% reduction in net IFNγ concentration in supernatants of α1(II)-stimulated PBMC cultures from baseline after 16 weeks of treatment. Because 10-20% of placebo-treated subjects are expected to experience reduction in IFNγ≥50%, the null hypothesis is that response rate to the treated group is equal to 20% versus the alternative that the response rate of the treated group is not equal to 20%. Data will be analyzed with chi-square tests or Fisher's exact test as appropriate. For the primary outcome variable the initial alpha level is 0.05. However, this level will be reduced to 0.0125, using the method of Bonferroni, because of the series of planned interim analyses.

Analysis of Secondary Outcome Variables.

This study has a completely randomized design, with subjects as random experimental units. There are two factorially arranged fixed effects, which are time (i.e., baseline, 8 weeks and 16 weeks; for re-treatment phase 24 and 34 weeks) and dose of drug (0, 30, 300, and 1000 μg). Baseline values of the response variable of interest will be used as the covariate. Only pre-planned contrasts will be made between each specific dose group and the placebo group at the various assessment times. For continuous variables, data will be analyzed using the MIXED procedure of SAS so that the covariance structure of the repeated measures over time within the same subject can be appropriately modeled. Similarly for all-or-none response variables, data will be analyzed with GLIM-MIX, using the same statistical model. For HLA alleles, the association with presence or absence of a response (change from baseline) at 8 and 16 weeks (and at 24 and 34 weeks for re-treatment), ignoring dose and stratifying for dose, will be analyzed separately at each time with chi-square tests or Fisher's exact test or Mantel-Haentzel tests, as appropriate. For all secondary outcome variables, the alpha level is 0.01.

Specific Methods

Measurement of IgA, IgM and IgG Antibodies to Bovine CII and APL A12 by ELISA:

Microtiter plates will be coated with 1 μg/ml of bovine CII or APL A12 diluted with 0.145M potassium phosphate buffer, pH 7.6. After an overnight coating at 4° C., plates will be washed with 0.15M NaCl, 0.05% Tween 20. Patient sera will be diluted in ELISA buffer (0.1M Tris, 0.15M NaCl, 0.05% Tween 20, pH 7.4) and added to coated microtiter plate wells for 2 h at 4° C. Plates will then be washed and incubated for 2 h at 4° C. with peroxidase-conjugated goat anti-human IgG Fc, or goat anti-human IgM or goat anti-human IgA Fc (Cappel Laboratories). The plates will be developed with o-phenylenediamine substrate, and the absorbance will be read at 450 nm with a micro-ELISA Auto Reader MR580. This ELISA is routinely used in our laboratory to measure type II collagen antibodies in human sera. Anti-CII and anti APL A12 antibodies will be measured at baseline, and at the 16 week visit. Anti APL A12 antibodies will also be measured at 8 weeks.

Preparation of Bovine CII:

Cartilage CII will be isolated and purified as previously described from fetal calves obtained from a slaughter house.

Preparation of Bovine α1(II):

The bovine CII α chain will be prepared by carboxymethyl (CM)-cellulose chromatography of heat denatured collagens as described.

Anti-CCP Antibodies:

We will measure anti-CCP antibodies at baseline at 8, 16, 24, and 34 week visits. Anti-CCP antibodies will be measured in sera by commercially available ELISA. We have used this ELISA in the recently completed NIH oral CII study.

Th1/Th2 in 48 Hour and 144 Hour PBMC Culture Supernatant:

Th1/Th2 cytokines will be assayed for using BioRad's 27 multiplex cytokine assay (BioRad Laboratories, Rockville Center, N.Y. 11571). The 48 and 144 hour PBMC culture supernatants will be used in this assay. The advantage of the multiplex is that 27 cytokines/chemokines can be assayed on a single 60 μL supernatant sample. The Th1/Th2 cytokines are Th1=IL-2, IFNγ, TNFα, IL-12*p 70, GMCSF; Th2=IL-4, IL-5, IL-10, IL-13. The multiplex assay will be performed in the Molecular Core at the VAMC. The remaining cytokines/chemokines measured by the human 27 multiplex assay are IL-1β, IL-1ra, IL-6, IL-7, IL-8, IL-9, IL-15, Eotaxin, basic FGF, GCSF, IP-10, MCP-1, MIP-1α, MIP-1β, PDGF bb, RANTES, and VEGF. Several of these cytokines/chemokines were modulated in the preliminary in vitro by RA PBMC cultured with APL A12+α1(II). These include IL-1ra, IP-10, PDGF-bb, RANTES, IL-10, IFNγ, and TNFα, all involved in RA synovitis.

Th3 Cytokines:

Th3 cytokine, TGF-β1, -β2 and -β3 will be assayed in supernatants (R & D Systems) from 48 hour cultures of PBMC cultured in serum free EXVIVO medium.

Protocols

Detailed Clinical Protocol

Inclusion Criteria

Patients must meet the following criteria for participation in the study:
1. Male or female; age 18 years.
2. American College of Rheumatology (ACR) 1988 revised criteria for rheumatoid arthritis.
3. Onset of disease age 16 or older.
4. Onset of disease at least 3 months prior to enrollment.
5. RA patients ages 18-70 with RA of ≥3 month duration which in the opinion of the examining rheumatologist is "clinically stable" and will likely not require adjustment of doses of DMARDs, NSAIDs, prednisone or anti-TNFα therapies for the 16 weeks of the treatment phase of the study. Patient must have a DAS 28 of ≤3.2.
6. Patients must agree to discontinue all "herbal remedies" listed in the Appendix.
7. Women of childbearing age will be advised to use effective means of contraception for the treatment phase of the trial and for 90 days thereafter. They must have a negative urine pregnancy test at the randomization visit. (Required by the FDA.)
8. Men will be advised to use effective means of contraception for the treatment phase of the trial and for 90 days thereafter. (Required by the FDA.)

Exclusion Criteria 1
1. Inability to render an informed consent in accordance with institutional guidelines.
2. Participation in another clinical research study involving the evaluation of another investigational drug within 90 days of entry into this study.
3. RA patients on >7.5 mg prednisone a day.
4. RA patients with intra-articular corticosteroid injections during the previous 30 days.
5. Concurrent serious medical condition which in the opinion of the investigator makes the patient inappropriate for the study.
6. Positive urine pregnancy test.
7. Age 71 years or greater.
8. Use of "fish oil" within the previous 4 weeks.
9. Therapy consisting of auranofin or cyclophosphamide (all other DMARDs are allowed).
10. Previous autologous or heterologous stem cell transplantation.
11. Active malignant neoplasm or past treatment consisting of antineoplastic drugs or total lymphoid irradiation.
12. Use of oral CII within the past one year. (Since oral tolerance is short-lived, we will permit patients in the study who have been off oral CII for >1 year.)
13. Diabetes Mellitus requiring medication.
14. Serum creatinine ≥2.0 mcg/dL.
15. An α1(II) IFNγ value <100% of the PBS IFNγ value within one month or less prior to the baseline visit and less than 50% reduction in APLA12+α1(II) IFNγ from α1(II) IFNγ concentration.

Patients meeting the above entrance criteria will be randomized to Groups 1, 2, 3, or 4.

Sample Base Size and Duration:

Patients with RA (DAS 28≤3.2) are relatively common. We feel confident that we will be able to enroll 40 patients for this study assuming ~20% dropout rate to have 32 completers. Patients will be recruited from rheumatology clinic at the Veterans Administration Medical Center, Memphis which serves a veteran population in the Mid South (Last year 27,357 Veterans were treated at the Memphis VAMC). We are currently following 200 Veterans with RA.

The feasibility of completing the study will depend on effective methods of recruitment or availability of patients and their willingness to complete the study. The treatment phase of the study has been designed to last 16 weeks with patients returning at week 24 for an 8 week post treatment follow-up visit. Considerable effort will be made to ensure complete and accurate ascertainment of clinical and intermediate outcomes. Clinic visits will be kept to a minimum frequency and duration. We will plan to screen and enroll patients for 3 years. From screening to completion of the post-treatment toxicity visit patients will spend 28 weeks in the study and an additional 8 weeks if they have an improvement ≥an ACR 20 or have ≥50% decrease in net IFNγ concentration in supernatants of α1(II)-stimulated PBMC cultures from baseline net IFNγ α1(II) values.

Informed Consent:

Informed consent for screening and randomization will be obtained from all eligible patients.

Randomization, Assignment Blinding:

All clinic personnel and participants will be blinded to individual treatment assignments. Randomization duties will be assigned to the statistician. Laboratory technicians performing ELISA assays and the investigator will be blinded to the treatment type.

| | | |
|---|---|---|
| (23.8%) | Group 1 | APL A12 30 μg/day |
| (23.8%) | Group 2 | APL A12 300 μg/day |

| | |
|---|---|
| (23.8%) Group 3 | APL A12 1,000 µg/day |
| (28.6%) Group 4 | Placebo |

General Screening:

Interested patients from the Memphis VAMC Rheumatology Clinic will be screened by study rheumatologists and demographic information will be supplied to the Study Coordinator who will contact the patient by phone and discuss the study in greater detail if necessary. The coordinator will complete a telephone screening form and review the chart for exceptions to inclusion/exclusion criteria. Eligible patients will be given an appointment for Visit 1 (screening).

Study Registration:

Patients who sign informed consent at Visit 1 and meet eligibility requirements at Visit 2 will be randomized to a trial arm by the Randomization Physician. 42 patients will be recruited and randomized to assure that ~8 patients will complete each of the treatments.

28 of 5.1 or incremental increase of >1.2 units points above entry DAS, or develop manifestations of other autoimmune diseases, they will be dropped from the study and the DMC, IRB, and FDA will be notified. The DMC will advise Dr. Postlethwaite whether to put a hold on the study.

Adverse Event Monitoring:

See description under "Safety Monitoring" above.

Visit 1 Screening: −4 Weeks

Patients will sign a Consent Form and will allow 15 mL blood to be obtained by venipuncture (two 10 ml tubes containing EGTA which actually draw 7.5 mL of blood) which will be sent to Dr. Postlethwaite at the Memphis VAMC for determination of PBMC immune response to α1(II), and 12½ ml blood for screening complete blood count and chemistry profile. A routine urinalysis will be done. A medical history and concomitant medication history will be obtained. Patients meeting the inclusion/exclusion criteria requirements will proceed to visit 2.

VISITS 1-9
Summary of Visits

| | Time (weeks) of study | | | | | | | |
|---|---|---|---|---|---|---|---|---|
| | −4 weeks Screen V-1 | 0 weeks Baseline V-2 | After 1 week† V-3 | After 4 weeks V-4 | After 8 weeks V-5 | After 16 weeks V-6 | Week 24 8 week post-treatment Final Toxicity V-7 | Week 26** V-8** | Week 34** V-9** |
| Consent | X | | | | | | | | |
| History and Physical Exam | X | X | | X | X | X | X | | X |
| Tender Joints | X | X | | X | X | X | X | | X |
| Inclusion/Exclusion | X | X | | | | | | | |
| Swollen Joints | X | X | | X | X | X | X | | X |
| MHAQ | | X | | X | X | X | X | | X |
| Physician's Global Assessment | | X | | X | X | X | X | | X |
| Patient's Global Assessment | | X | | X | X | X | X | | X |
| Adverse Events | | | X | X | X | X | X | | X |
| Study Medication History | | | X | X | X | X | X | | X |
| Concomitant medication history | X | X | X | X | X | X | X | | X |
| CBC, UA | X | X | X | X | X | X | X | | X |
| Blood Chemistry | X | X | X | X | X | X | X | | X |
| PBMC Immunity | X | X | | | X | X | X | | X |
| Study Drugs Dispensed | | X | | X | X | | | X** | |
| Misoprostol Dispensed* | | X | | X | X | | | X** | |
| Urine Pregnancy Test | | X | | X | X | X | X | | X |
| ESR | | X | | X | X | X | X | | X |
| CRP | | X | | X | X | X | X | | X |
| Albumin | | X | | X | X | X | X | | X |
| Rheumatoid Factor | | X | | X | X | X | X | | X |
| DAS 28 | | X | | X | X | X | X | | X |
| Anti CCP and Anti-CII | | X | | | X | X | X | | X |
| Anti APL A12 | | X | | | X | X | X | | X |

*To participants taking NSAIDS
**To patients having ≥ ACR 20 response or immune response ≥50%↓ in net IFNγ concentrations in α1(II)-stimulated PBMC culture supernatants from baseline will return 2 weeks after Week 24 to take 8 additional weeks of study drug.
†HLA Determination Clinical trial participants will be followed through regularly scheduled examinations to collect data on study variables, to monitor the occurrence of possible adverse effects, and to promote adherence to the study protocol. Patients will be seen at a screening visit and 6 times during the 24 week study. Patients with ACR of 20 or greater improvement or have a ≥50% decrease in net IFNγ concentration in supernatants of α1(II-stimulated PBMC) at 16 weeks will be re-administered their placebo or APL A12 dose for weeks 26-34. Blinding will be maintained during the retreatment phase.

Stopping Rules:

If patients develop hypersensitivity reactions (hives, itching, wheezing, synocope), if their arthritis flares with a DAS Visit 2: Week 0—Baseline Patients will be randomized to Group 1 (APL A12 30 µg), Group 2 (APL A12 300 µg), Group 3 (APL A12 1,000 µg) or Group 4 (Saline placebo).

Patients will have complete history and physical examination performed, number of tender and swollen joints, MHAQ, Physician's Global Assessment and Patient's Global Assessment recorded. A DAS 28 form will be completed.

Patients will have blood in a "5 mL Red Top Tube" (4 ml) for serum collected for anti-CII, anti APL A12 and anti CCP antibody level determinations. This will be collected after blood clots for 1 hour at room temperature and stored at −20° C.

Patients will have 35 mL blood obtained in five 10 ml "EGTA tubes" to be sent to Dr. Postlethwaite for PBMC response to α1(II), APL A12, and anti CD3/CD28 microbeads in assays in Objectives 1 and 2.

Patients will be given a 4-week plus 14-day supply of study medication which they will take every day.

Patients will have 15 mL blood drawn for CBC, albumin, ESR, CRP, rheumatoid factor, aspartate aminotransferase (AST), alanine aminotransferase (ALT), alkaline phosphatase, bilirubin, $Na^+$, $K^+$, $Cl^-$, $HCO_2^-$, BUN, creatinine and urine obtained for urinalysis. Women of childbearing age will have a urine pregnancy test performed.

Misoprostol 100 μg will be provided by the VAMC Pharmacy to be dispensed to patients taking NSAID drugs to be taken orally every 12 hours. Patients will be instructed to bring their misoprostol supply to the Study Coordinator at each follow up visit to be counted for compliance reasons. The misoprostol will be returned to the patient after counting.

Patients will take the $1^{st}$ dose of study medication and misoprostol, if required, and will be observed in the clinic for 2 hrs for appearance of anaphylactic symptoms. The clinic is equipped with a "crash cart".

Visit 3: Week 1

Patients will be asked about "adverse events". Patients will be asked about changes in DMARD, NSAID or prednisone doses and joint injections and whether they have taken study medications as instructed.

Patients will have 15 mL blood drawn for AST, ALT, alkaline phosphotase, bilirubin, CPK, BUN, creatinine, CBC, albumin, $Na^+$, $K^+$, $Cl^-$ and $^-HCO_2$ and urine obtained for urinalysis.

Visit 4: Week 4

Patients will have number of swollen and tender joints, DAS, H/P, MHAQ, Physician's Global assessment and Patient's Global assessment determined and a DAS form completed.

Patients will be asked about "adverse events". Patients will be asked about changes in DMARD, NSAID or prednisone doses and joint injections and whether they have taken study medications as instructed.

Patients receive a 4-week plus 14-day supply of study medication.

Patients will have 15 mL blood drawn for CBC, albumin, ESR, CRP, rheumatoid factor, AST, ALT, alkaline phosphatase, bilirubin, $Na^+$, $K^+$, $Cl^-$, $HCO_2$, BUN, CPK, creatinine and urine obtained for urinalysis. Women of childbearing age will have a urine pregnancy test performed.

Patients on NSAIDs will receive a 4-week plus 14-day supply of misoprostol 100 μg to be taken every 12 hrs.

Visit 5: Week 8 (Groups 1, 2, 3 and 4)

Patients will have a complete history and physical examination and number of swollen and tender joints, MHAQ, Physician's Global Assessment, and Patient's Global Assessment determined and a DAS 28 form completed.

Patients will be asked about "adverse events". Patients will be asked about changes in DMARD, NSAID or prednisone doses and joint injections and whether they have taken study medications as instructed.

Patients will have 35 mL blood drawn into five 10 ml EGTA tubes which will be sent to Dr. Postlethwaite at the Memphis VAMC for quantitation of PBMC immune response to α1(II), APL A12 and anti-CD3/CD28 microbeads. 5 ml blood (red top tube) will be obtained for anti-APL A12 antibodies.

Patients will have 15 mL blood drawn for CBC, albumin, ESR, CRP, rheumatoid factor, AST, ALT, alkaline phosphatase, bilirubin, $Na^+$, $K^+$, $Cl^-$, $HCO_2$, CPK, BUN, creatinine and urine obtained for urinalysis. Women of childbearing age will have a urine pregnancy test performed.

Patients will be given an 8-week plus 14-day supply of study medication.

Patients on NSAIDS will receive an 8 week+14 day supply of misoprostol 100 μg to be taken every 12 hours.

Visit 6: Week 16 (Groups 1, 2, 3 and 4)

Patients will have a complete history and physical examination and number of swollen and tender joints, MHAQ, Physician's Global Assessment, and Patient's Global Assessment determined and a DAS 28 form will be completed.

Patients will be asked about "adverse events". Patients will be asked about changes in DMARD, NSAID or prednisone doses and joint injections and whether they have taken study medications as instructed.

Patients will have 35 mL blood drawn into five 10 ml EGTA tubes which will be sent to Dr. Postlethwaite for quantitation of PBMC immune response to α1(II), APL A12 and anti CD3/CD28 microbeads.

Patients will have 15 mL blood drawn for CBC, albumin, ESR, CRP, rheumatoid factor, AST, ALT, alkaline phosphatase, bilirubin, $Na^+$, $K^+$, $Cl^-$, $HCO_2$, CPK, BUN, creatinine and urine obtained for urinalysis. Women of childbearing age will have a urine pregnancy test performed.

Patients will have blood drawn in a 5 mL red top tube for serum collected for anti-CII antibody, anti-APL A12 and anti-CCP antibody level determinations. This will be collected after blood clots for 1 h at room temperature and stored at $-20°$ C.

Visits 7: 24-Week Treatment Follow-Up—Toxicity Check (All Groups)

As required by the FDA, patients will return again at week 24 (8 weeks post treatment/24 weeks from baseline) for final evaluation. Patients in all Groups will be evaluated for safety by 1) complete physical examination; 2) routine complete blood counts, urinalysis, chemistries (electrolytes, glucose, BUN, creatinine, CPK, total bilirubin, AST, alkaline phosphatase, and ALT). Three 10 mL EGTA containing and 1 (5 mL) red top tubes of blood will be obtained for immunology studies. (Anti-APL A12 antibodies, anti CII antibodies, and cytokine profiles in PBMC cultures stimulated with APL A12 and CII). A detailed listing of the medications they have used since week 16 visit will be recorded. These immunology tests will be performed to assess prolonged effects of APL A12 on the immune system and to promote a second baseline to anyone re-treatment effects of APL A12 at visits 8 and 9 (Weeks 26, 34, respectively).

Retreatment of ACR 20 Responders and/or Immune Responders:

Patients who have an ACR 20 response or immune response i.e. 50% reduction in net IFNγ concentration in supernatants of α1II-stimulated PBMC from baseline at week 16 will be retreated with the study medication or placebo they were randomized to take. This is being done to determine whether net α1(II) IFNγ concentration from week 16 values will increase and/or whether arthritis will flare upon retreatment. The approach will be to re-administer the study medication (whatever dose of APL A12 they were randomized to receive, or placebo if they were randomized to receive placebo) for an additional two months. Two months should be enough retreatment to determine whether enhanced net IFNγ α1(II) concentration in supernatants of α1(II)-stimulated PBMC cultures or flare of RA will be induced. Since most clinical trials involving RA patients have a 15-20% placebo ACR 20 response, we anticipate having at least 20% of 24 APL A12 patient completions (or at least five patients) who will be retreated with APL A12. However, we would expect a greater number of patients than five because we anticipate a larger number will have an immunologic response and possibly a clinical response.

Visit 8: Week 26 (Groups 1, 2, 3, 4)

Patients qualifying (see above) for the retreatment phase will be given an 8 week+14 days supply of study medication.

Patients on NSAIDS will receive an 8-week plus 14-day supply of misoprostol 100 μg to be taken every 12 hours.

Visit 9: Week 34 (Groups 1, 2, 3, 4)

Patients will have a complete history and physical examination and number of swollen and tender joints, MHAQ, Physician, Global Assessment, and Patients' Global Assessment determination and a DAS 28 form will be completed.

Patients will be asked about "adverse events". Patients will be asked about changes in DMARD, NSAID or prednisone doses and joint injection and whether they have taken study medications as instructed.

Patients will have 25 ml blood drawn into three "EGTA containing 10 ml tubes" which will be sent to Dr. Postlethwaite for quantitation of PBMC (immune response to α1(II)), APL A12 and anti-CD3/CD28 microbeads.

Patients will have 15 mL blood drawn for CBC, albumin, ESR, CRP, rheumatoid factor, AST, ALT, alkaline phosphatose, bilirubin, $Na^+$, $K^+$, $Cl^-$, $HCO_3$, CPK, BUN, creatinine and urine obtained for urinalysis. Women of childbearing age will have a urine pregnancy test performed.

Patients will have blood drawn in "5 ml Red Top Tube" for serum collected for anti-CII antibody, anti-APL A12 and anti-CCP antibody level determination. This will be collected after blood clots for 1 hour at room temperature and stored at −20° C.

Chemistry, Manufacturing, and Control Data

HC Peptide 1 and Saline Placebo: The same lot (Number 2K08036) of APL A12 (HC Peptide 1) will be used in this protocol. A portion of HC Peptide 1 will be transferred using sterile technique from stock bottles received from the manufacturer. The HC Peptide 1 powder will be placed into a sterile 120 mL Nalgene polypropylene bottle previously weighed to determine its tare weight. To prepare a saline solution of HC Peptide 1 sterile IV grade physiologic saline (Baxter) will be added using sterile technique. To prepare a working stock IV saline will be added to the weighed peptide to affect a final concentration of 1 mg/mL which will be sterilized by filtration through Nalgene 0.45 micron filter #450-0045. Concentration of APL A12 in the filter sterilized working stock solution will be determined by BLA Protein Assay (Pierce, Thermo Scientific, 23225). Portions of the working stock APL A12 peptide solution will be diluted with sterile Baxter 0.9% Sodium Chloride to containing 0.5 mg/mL, 150 ug/ml and 15 ug/ml HC Peptide 1 Solutions. Aliquots (2 ml) of each of the 3 HC Peptide I stocks or placebo (sterile IV saline) will be transferred using sterile technique into sterile polypropylene 2 ml screw top Nalgene vials (#5012-0020), the tops screwed on firmly, and placed upright in test tube racks, frozen at −20° C. for overnight and placed 35/1 quart ZIPLOC®-sealable plastic bag. Patients will carry the HC Peptide 1 or Placebo home in the "6 pack cooler" ice chests containing ice. Each bag will contain Nalgene vials, a 4-weeks plus 7-days supply of HC Peptide 1 or Saline placebo. The patients will be given 1 bag (4-weeks plus 7-days supply) of HC Peptide 1/Saline Placebo at week 0 and week 4 visit. They will also be given individually wrapped sterile polypropylene medicine transfer pipettes. Each morning within 30 minutes before eating breakfast, patients will remove a sterile transfer pipette from its plastic case and draw up the HC Peptide 1 or Placebo to the 2 mL mark on the medicine dropper syringe depositing the 2 mL content into their mouth. They will swallow the contents and chase with a 4 ounce glass of water. The one bag of study medication dispensed at week 0 and week 4 visits and one bag at week 8 and 26 visits will be stored in the subject's refrigerator. The second bag of study medication dispensed at week 8 and week 26 visits will be stored for 28 days in the freezer of the study subject after which it will be placed in the refrigerator for thawing so it can be used for weeks 13-16 and weeks 31-34.

Pharmacology and Toxicology Data

1. Animal Data

Mode of Action of HC Peptide 1:

The mode of action of HC Peptide 1 is not completely understood; however, work in our laboratory with CII related analog/altered peptide ligands suggest the likely mode of action would be for HC Peptide 1 to be presented in the context of MHC Class II by antigen presenting cells to T cells ($CD4^+$ and/or $CD8^+$ T cells) and be incorporated into the MHC-peptide-TCR complex. HC Peptide 1 would probably activate altered signaling within the T cell resulting in suppression of Th1 cytokines (e.g. IFNγ, TNFα, GMCSF, IL-2) and enhanced Th2 cytokines (IL-10, IL-4) and perhaps Th3 (i.e. TGFβ) synthesis. The secreted Th2 and Th3 cytokines may exert a bystander effect and suppress Th1 cytokine production by neighboring $CD4^+$ T cells. The changes induced by HC Peptide 1 in cytokine production from Th1 to Th2/Th3 types are supported by in vitro studies using cultured PBMC from patients with RA.

One of the most important characteristics of the A12 analog peptide is its ability to reduce a Th1 cytokine profile and induce a Th2-type cytokine secretion profile in humans and in DR1 transgenic mice. In work we have published, DR1 transgenic mice were immunized with A12 peptide or CII emulsified with CFA. Culture of the immune T cells with various antigens showed that the cells from mice receiving A12 secreted predominantly Th2 cytokines in response to itself or α1(II) while their response to PPD was Th1 (48). In contrast, cells from mice immunized with CII generated multiple cytokines, but predominantly a Th1 response to the wild-type peptide. Importantly, although immunized with CII, they responded to A12 with only a Th2 response. These data make it clear that cells previously primed with CII will secrete a full range of cytokines in response to A2, but only the Th2 cytokines in response to A12.

Together, these data suggest that a population of cells can be induced that respond to the A12 peptide with a predominantly Th2 phenotype. The ability to induce the secretion of Th2 cytokines may explain the profound suppressive effects A12 has on the development of CIA. A single lot (2K08036) of APL A12 (HC Peptide 1) of 3 grams has been purchased from NeoMPS for this clinical trial.

Early T Cell Signaling with A2 and A12:

Purified CD4+ cells from the DR1-TCR tg mice are an excellent source of cells to explore the intracellular signaling pathways induced by either A2 or A12. In preliminary experiments we precipitated proteins with an antibody specific for CD3-ζ (34) to examine for the presence of phosphorylated proteins. As expected, culture with the wild type (A2) peptide induced strong TCR-ζ chain phosphorylation associated with phosphorylation of Zap-70. On the other hand A12 did not significantly activate TCR-ζ (FIG. 4).

Figure 4:
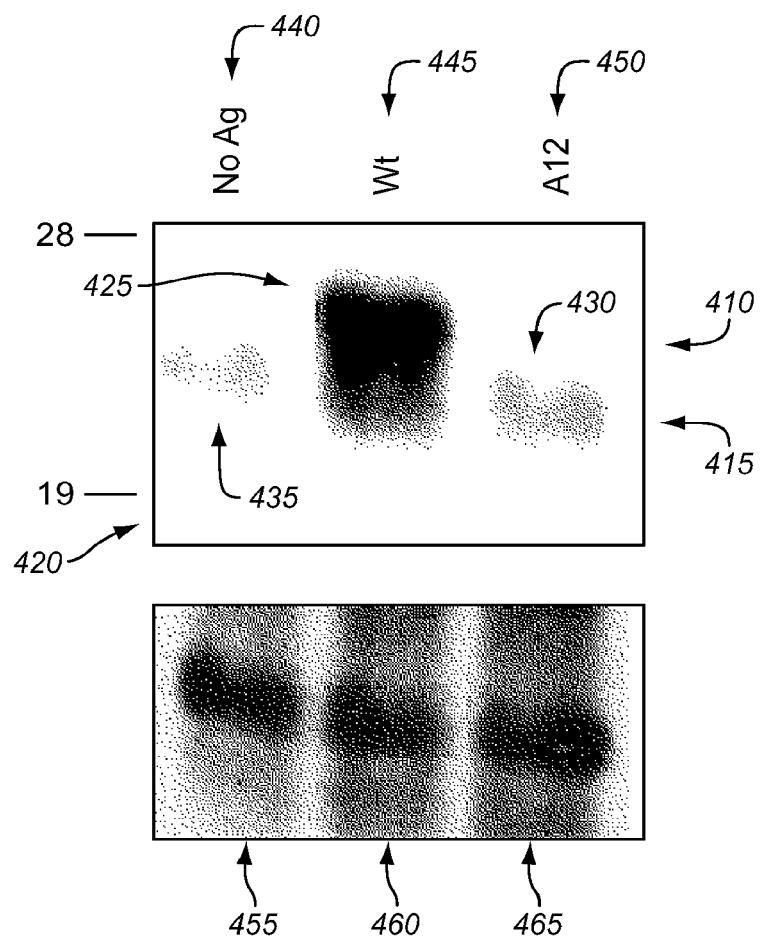
FIG. 4 shows phosphorylation of the TCR-ζ chain.

FIG. 4 shows phosphorylation of the TCR-ζ chain CII-specific. CD4+T cells were cultured with APC's pulsed with the wild-type peptide (WT), A12, or no antigen (No Ag).

Proteins were immunoprecipitated with 3 mg of affinity-purified anti-TCR-ζ antibody. The immunoprecipitates were separated by SDS-12%-PAGE, and transferred to nitrocellulose membrane. The membrane was blotted with monoclonal anti-phosphotyrosine antibody (α-pTyr). The positions of the phosphorylated-TCR-ζ are shown by arrows 410, 415. The 21 kDa and 23 kDa bands were not detected in immunoprecipitates from a B cell lymphoma line (data not shown). Bands for the total amount of zeta protein were identical for all three columns. Arrows 410 and 415 are shown denoting 21 kDa and 23 kDa bands, respectively. Axis 420 shows kDa band location. The bands are for No Ag 440, Wt 445, and A12 450. The bands are shown: Wt 425, No Ag 435, A12 430. Bands for zeta protein are shown: No Ag 455, Wt 460, and A12 465.

Figure 8A:
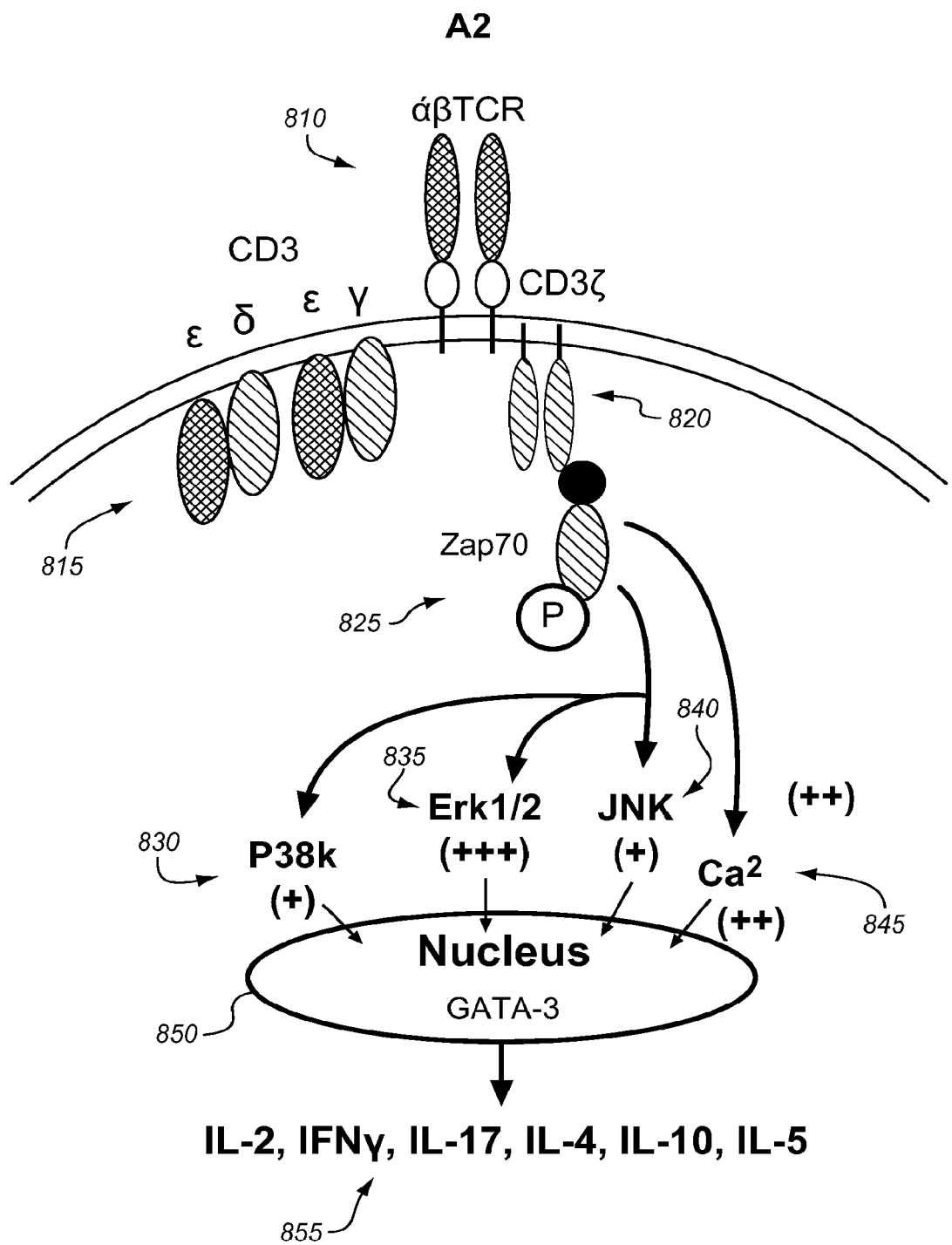
FIGS. 8A and 8B show a potential representation of signaling initiated by A12.
Figure 8B:
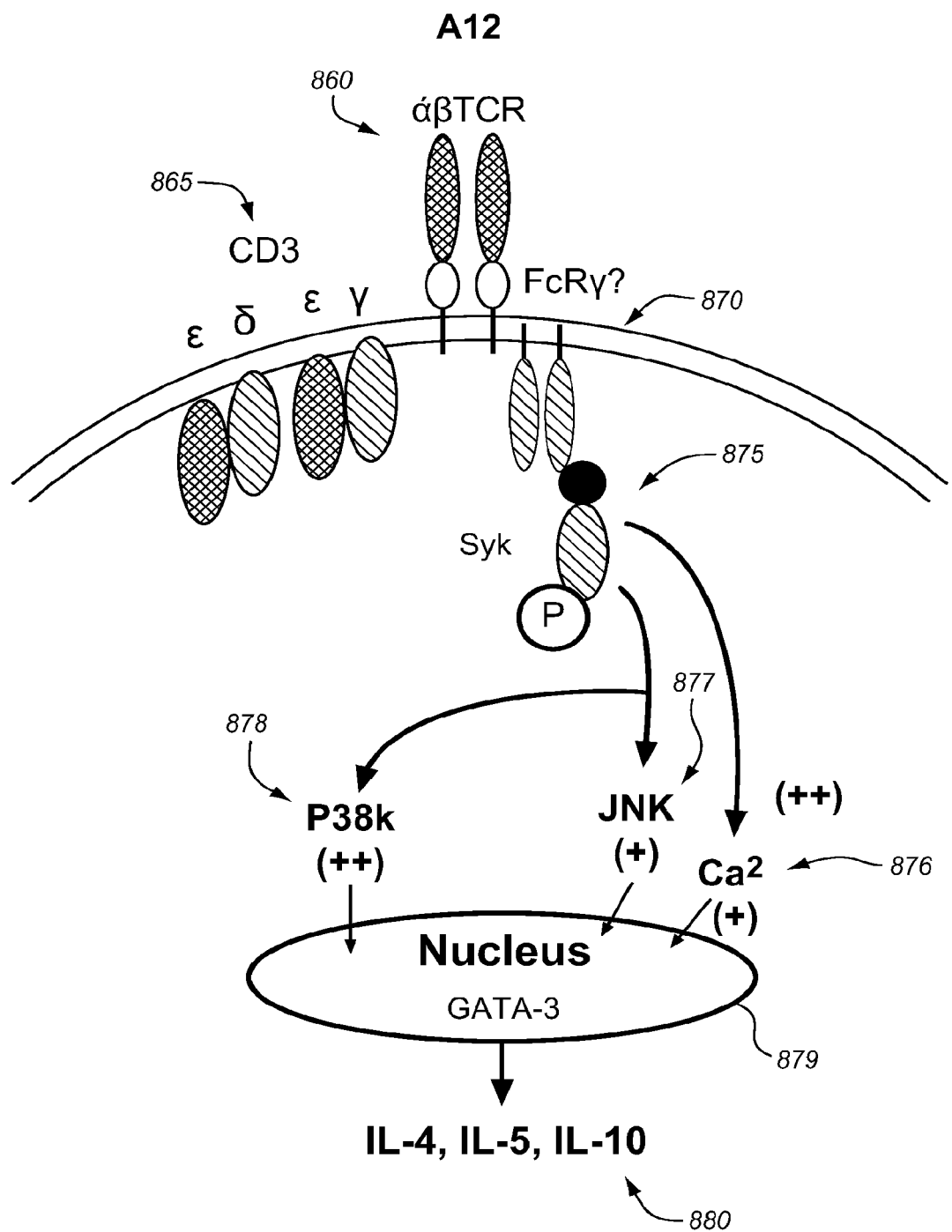

Evidence that A12 Activates Spleen Tyrosine Kinase (Syk):

Since T cells clearly responded to A12 differently than to the wild type A2 peptide, we analyzed them for the possibility that they might be utilizing an alternative signaling pathway. Spleen tyrosine kinase (Syk), a kinase ordinarily utilized by B cells was selected for further analysis. In these experiments, CD4+ T-cells from the DR1/TCR transgenic mice were purified by negative selection (using a Miltenyi kit) and stained with an antibody specific for phospho Syk following exposure to APCs prepulsed with either A2 or A12. As shown in FIGS. 8A and 8B, the A12 peptide, but not A2, induced significant Syk phosphorylation compared with A2 and media controls. Histograms were generated using flow cytometry with gating specifically on the CD4+ population, confirming that the changes observed were produced by T-cells. When the same cells were stained with an antibody specific for phospho-Zap-70, A12 had little effect, while A2 induced significant Zap-70 phosphorylation, confirmed by flow cytometry (data not shown).

Figure 5A:
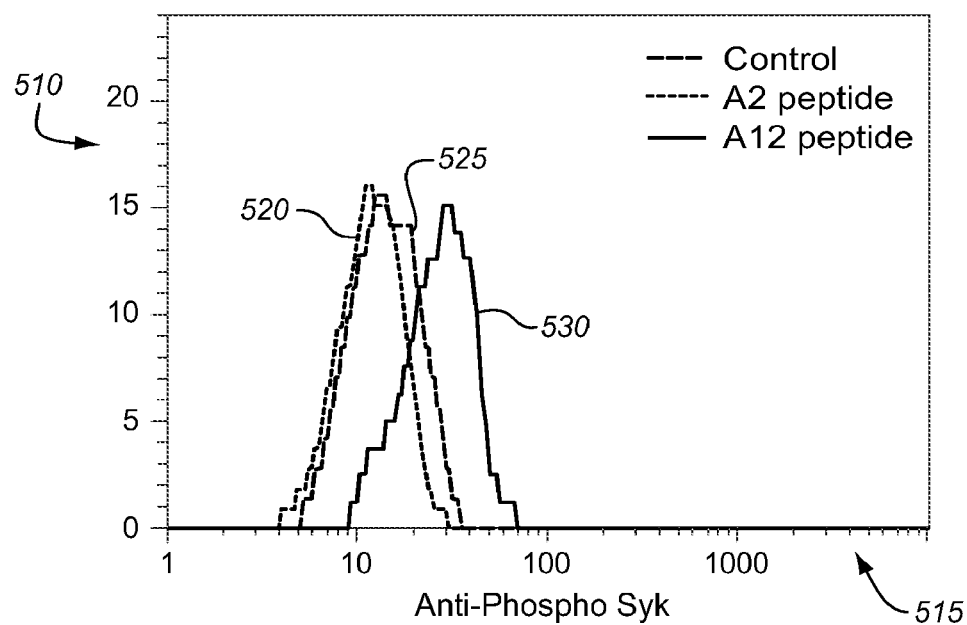
FIGS. 5A and 5B show T cell signaling induced by A2 and A12.
Figure 5B:
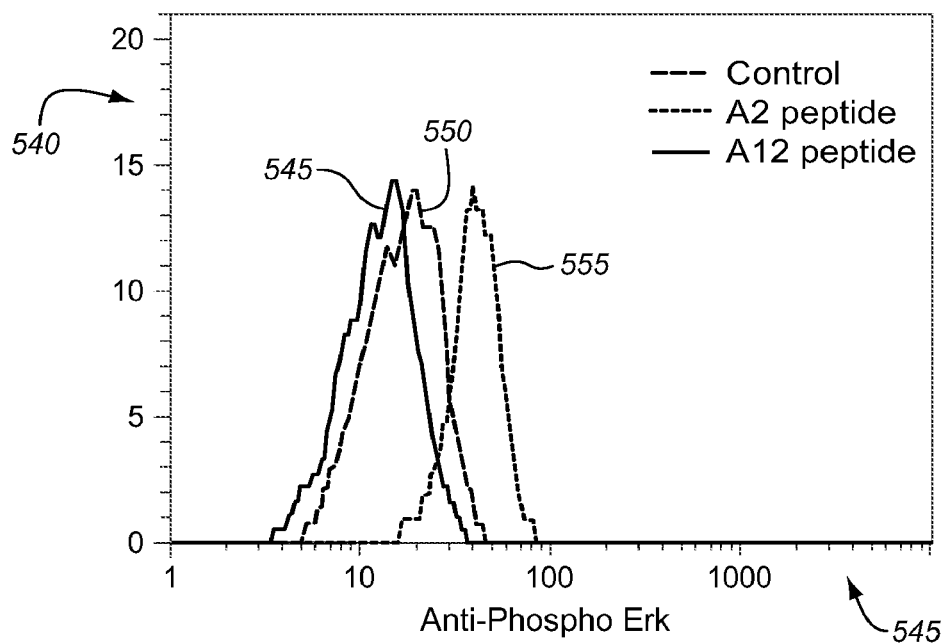

Evidence that A12 Causes Signaling Through an Alternative Pathway:

Because mitogen-activated protein kinases (MAPKs) are thought to play a central role in the transmission of membrane receptor signals to the nucleus, we investigated the kinetics and duration of ERK, a MAPK critical for T cell responses. Our data show that ERK is activated following exposure to APCs pulsed with the wild type A2 peptide but not A12 (FIG. 5A-B). Again a CD4+ specific antibody confirmed that the changes observed were produced by T-cells. These data indicate that MAP kinase activation may be instrumental in determining the type of cytokines produced.

FIGS. 5A and 5B show T cell signaling induced by A2 and A12. Flow cytometry was performed using purified CD4+ T cells from spleens of DR1 TCR Tg mice. The T cells were stimulated by APCs pre-pulsed with A2, A12 or no peptide (Control) for 5 minutes. The cells were then fixed, permeabilized, and stained with an antibody specific for phospho-Syk (Tyr 323) (left panel) or phospho-ERK 1/2 (right panel) and analyzed by flow cytometry. Both plots are gated on CD4 T cells. Axes 510, 540, show the number of events and axes 515, 545 show a logarithmic scale for Anti-phospho Erk and Syk respectively, for FIGS. 5A and 5B. In FIG. 5A line 520 is for A2 peptide, line 525 is the control, and line 530 is the A12 peptide. In FIG. 5B line 545 is for A12 peptide, line 550 is the control, and line 555 is the A2 peptide.

Finally, we examined the expression of FcεRIγ, a molecule known to associate with the TCR complex. In some circumstances, the TCR is rewired so that the FcRgamma chain assumes the function of the zeta chain. Therefore, the DR1 TCR tg cells were cultured with either A12, or A2, or media alone and stained with an antibody specific for the gamma chain of the FcεRIγ molecule. As shown in FIG. 6, the cells stimulated with A12 had a significant increase in the FcR gamma chain, while cells cultured with A2 were not different from those treated with media alone. Taken together, these studies demonstrate conclusively that A12 utilizes very unique T cell signaling molecules.

These preliminary studies set the stage for more extensive investigations of the TCR intracellular signaling differences set in motion by exposure to either A2 or A12-pulsed APCs. In the next few paragraphs we include experiments utilizing another collagen-specific TCR—which is restricted by the murine I-A$^q$ in order to demonstrate our expertise in using the techniques necessary to complete the work proposed.

Data from a DBA/1 Transgenic Mouse that Supports the Hypothesis that A12 Acts by Signaling through Syk:

In previous work we have used an APL (A9) that interacts with mouse I-A$^q$ in a manner similar to that of A12 for DR1 and DR1. The transgenic mouse used for these studies is called qCII24. We assumed that the analog A9 activated an alternate signaling pathway, bypassing the TCR-ζ-Zap-70 pathway activated by wild type ligand (A2) and triggered different downstream MAP kinases. CD4+ T-cells from qCII24 mice were treated with piceatannol (30 μm), a Syk inhibitor, for 1 hour and stimulated with APCs pulsed with A2 or A9 for 30 minutes. Stimulation of the T-cells with A9 resulted in the phosphorylation of p38; however, when piceatannol was added, p38 phosphorylation was blocked (FIG. 7A-D). As anticipated, activation of the T-cells with A2 peptide resulted in strong phosphorylation of ERK, which was unaffected by piceatannol.

Figure 7A:
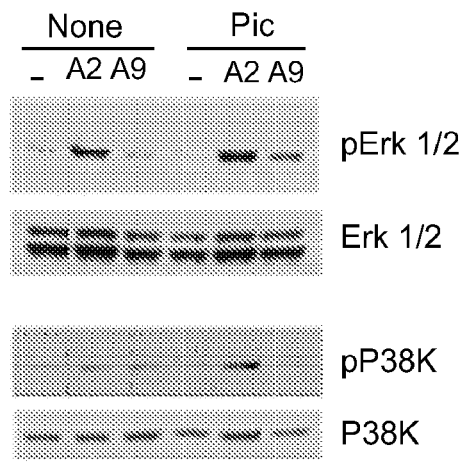
FIGS. 7A-7D show inhibition studies.
Figure 7B:
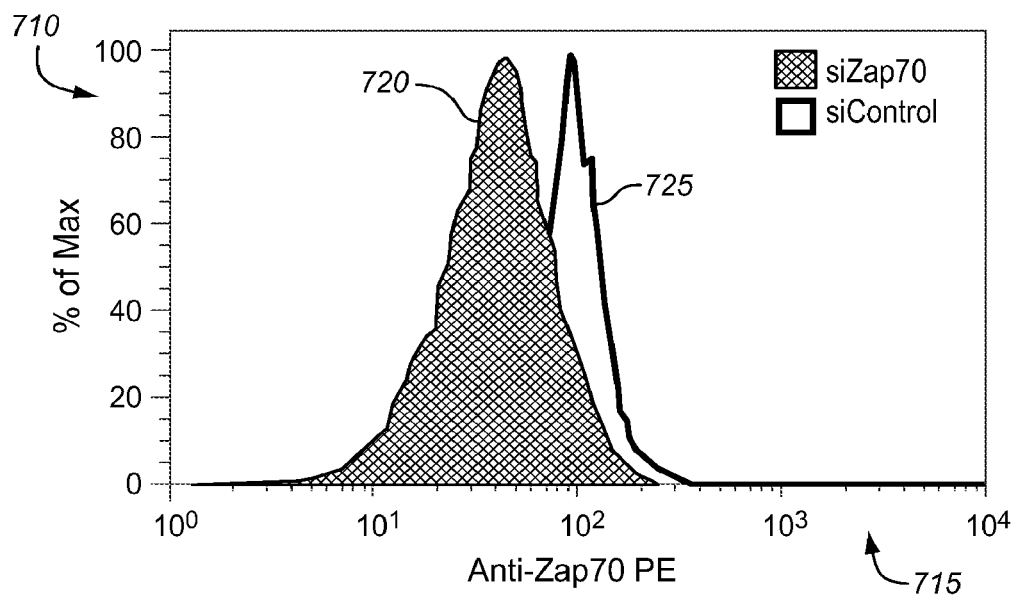
Figure 7C:
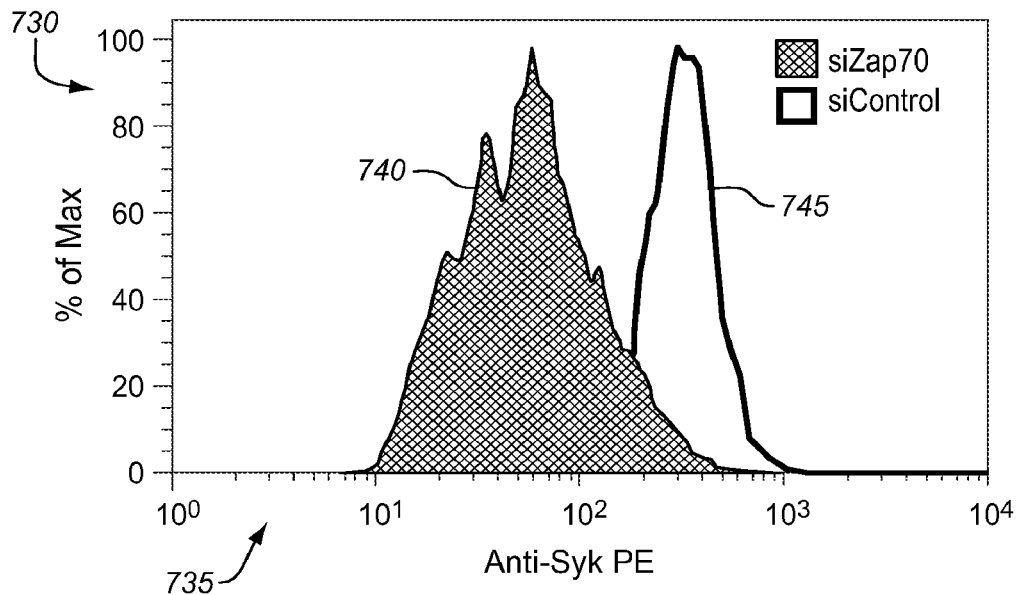
Figure 7D:
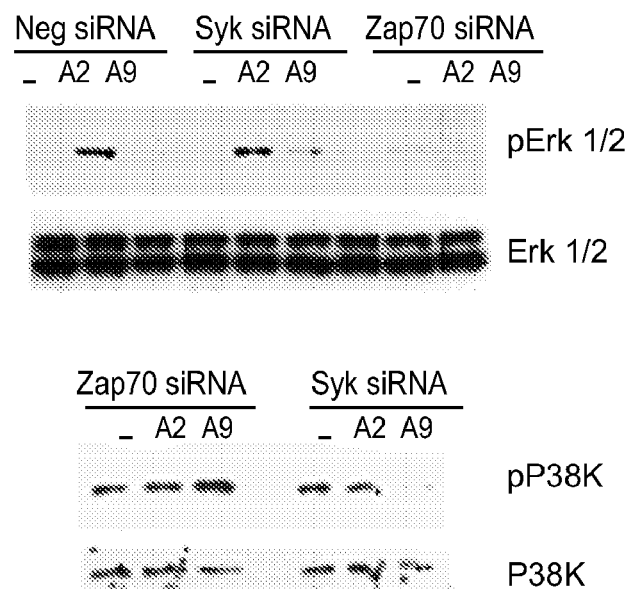

In FIGS. 7A-7D, inhibition studies are shown. In FIG. 7B, axis 710 is for the percentage of the maximum and axis 715 is for anti-Zap70 PE; line 720 is for Zap70, and line 725 is for Control. In FIG. 7C, axis 730 is for the percentage of the maximum and axis 735 is for anti-Syk, line 740 is for siSyk, and line 745 is for Control. Inhibition studies. In FIG. 7A, CD4+T cells from qCII24 mice were cultured with 30 μg piceatannol (Pic), an inhibitor of Syk, for 1 hour and stimulated for 10 minutes using antigen presenting cells pre-pulsed with A2 or A8, or no peptide (–). The whole cell lysates were subjected to immunoblotting as described in Materials and Methods using an antibody specific for phospho-Erk 1/2 (pErk) or an antibody against phospho-p38K (pP38K). The same membrane was also stripped and re-probed with antibodies against total Erk or total p38k protein. In FIGS. 7B and 7C, verification of the efficiency of the knock-down for gCII24 transgenic T cells were transfected with siRNAs for Zap70 (siZap 70), Syk (siSyk) or an unrelated siRNA (siControl). Efficiency of the knock-down was verified using antibodies which recognize either Zap 70 (lower panel) or Syk (upper panel). Flow cytometry was performed with histograms gated on CD4+ T cells to confirm that the total amount of either the Zap-70 protein or the Syk protein in CD4+ T cells was decreased in comparison with the unrelated control. In FIG. 7D CD4+ T cells from qCII24 mice were transfected with siRNA and exposed to antigen presenting cells pulsed with A2, A8 or no peptide (–). Cell lysates were subjected to Western blot analysis using anti-phospho antibodies against Erk (pErk) and P38K (pP38K). The same membranes were stripped and reprobed with antibodies to total Erk (Erk) or total P38K (P38K) as controls. For Erk phosphorylation the T cells were incubated with pre-pulsed APCs at 37° C. for 10 min. p38K phosphorylation. T cells were stimulated with pre-pulsed APCs at 37° C. for 30 minutes.

To confirm the importance of Syk in A9-induced signaling, we used siRNAs to Syk and Zap-70 to "knock down" Syk and Zap-70 respectively, and determine whether p38k and ERK were activated. CD4+ T-cells were transfected with siRNA and stimulated with pulsed APCs. ERK phosphorylation, normally induced by A2 peptide, was significantly reduced in cells transfected with Zap-70 siRNA; however, Syk siRNA was ineffective. Conversely, p38k activation by A9 was notably suppressed by Syk siRNA, but not by Zap-70 siRNA (FIG. 7A-D). These results show that A2 peptide causes T-cell activation through a conventional TCR-ζ-Zap-70 signaling cascade. To the contrary, A9 causes T-cell activation through an alternative Syk signaling pathway, resulting in the activation of a different set of MAPKs. In FIGS. 8A and 8B, we have diagrammed pathways we hypothesize to be involved in APL A12 (HC Peptide 1). FIGS. 8A and 8B provide diagram of our hypothesis concerning the signaling initiated by A12. To assist in understanding this diagram, the following is a listing of the constituents:

αβTCR—810, 860

CD3—815, 865

CD3ζ—820

Zap70—825

P38k—830, 878

Erk1/2—835

JNK—840, 877

$Ca^2$—845, 876

Nucleus GATA-3—850, 879

IL-2, IFNy, IL-17, IL-4, IL-10, IL-5—855

IL-4, IL-5, IL-10—880

Syk—875

FcRy?—870

HC Peptide 1 is effective in reducing CII induced arthritis in mice bearing a transgene for human DRB1*0401. See FIG. 4. HC Peptide 1 was most effective at the 50 μg/day dose given orally by gavage. We also found that IFNγ production by spleen cells was reduced by gavage by APL A12 (Table V). Administration of HC Peptide 1 APL A12 by gavage to DRB1*0401 transgenic mice down regulated production of IL-17 and upregulated production of IL-10 from isolated in Peyer's Patch cells cultured in vitro and stimulated by APL A12 (Table VI).

TABLE IV

Immunization of DR1 Transgenic Mice with either CII or Analog Peptide A12

| Immunogen | Antigen | IFN-γ (pg/ml) | IL-10 (pg/ml) | Il-4 (pg/ml) |
|---|---|---|---|---|
| CII | Wild-type Peptide | 3,150 | 276 | 10 |
|  | A12 | 0 | 610 | 40 |
|  | PPD | 1,575 | 110 | 0 |
| Analog A12 | Wild-type Peptide | 175 | 792 | 23 |
|  | A12 | 0 | 808 | 31 |
|  | α1(II) | 0 | 680 | 45 |
|  | PPD | 2,225 | 248 | 0 |

Pooled splenocytes and lymph node cells from DR1 Transgenic mice immunized with either CII or Analog A12, 10 to 14 days previously, were adjusted to a concentration of $5 \times 10^6$ cells per ml and cultured with 100 μg/ml of indicated antigen. Supernatants were collected from 72 to 120 hours later and analyzed for the presence of IFN-γ, IL-4 or IL-10. Values are expressed as pg/ml.

TABLE V

Oral Administration of APL A12 to DR1 Transgenic Mice Down Regulates Production of IFNγ by Cultured Splenocytes*

| | IFNγ Levels in Splenocyte Culture (pg/mL) | | |
|---|---|---|---|
| Mice Gavaged | PBS | $CII_{263-270}$ | APL A12 |
| With PBS (n = 5) | 96 ± 63 | 280 ± 222 | 65 ± 52 |
| With $CII_{263-270}$ (n = 5) | 68 ± 85 | 124 ± 84 | 80 ± 52 |
| With APL A12 (n = 5) | 2 ± 3 | 12 ± 20 | 5 ± 10 |

*6-8 wk old DR1 transgenic mice were gavaged 8 times over 2 weeks with 100 μl sterile PBS, or 100 μl PBS containing 50 μg $CII_{263-270}$ peptide, or 100 μl PBS containing 50 μg APL A12. Mice were immunized with 100 μg native bovine CII in a CFA emulsion and after 2 weeks were sacrificed. The splenocytes were prepared and setup in culture with PBS, wild type human $CII_{263-270}$ peptide (the immunodominant epitope of CII in DR1 transgenic mice) or with APL A12 at a concentration of 50 μg/ml.

TABLE VI

Oral Administration of APL A12 to DR1 $TCR_{tg}$+/+ Mice Down Regulates IL-17 and Up Regulates IL-10 in Cultures of Peyer's Patch Cells*

| | Cytokine Levels in Peyer's Patch Cultures (pg/mL) | | |
|---|---|---|---|
| Mice Gavaged | PBS | $CII_{263-270}$ | APL A12 |
| | IL-17 | | |
| With PBS (n = 5) | 16 | 30 | 16 |
| With $CII_{263-270}$ (n = 5) | 11 | 256 | 62 |
| With APL A12 (n = 5) | 2.4 | 2.4 | 1.8 |
| | Il-10 | | |
| With PBS (n = 5) | 17 | 45 | 27 |
| With $CII_{263-270}$ (n = 5) | 15 | 15 | 35 |
| With APL A12 (n = 5) | 116 | 94 | 105 |

*6-8 wk old DR1 CII-specific TCR transgenic mice (DR1 $TCR_{tg}$+/+) were gavaged 9 times over 2 weeks with 100 μl PBS, or 100 μl PBS containing 50 μg $CII_{263-270}$ peptide, or 100 μl PBS containing 50 μg APL A12. Four hours after the last gavage, mice were sacrificed. The Peyer's Patch cells were isolated and cultured for 3-5 days with PBS $CII_{263-270}$ (50 μg/ml) or APL A12 (50 μg/ml). Aliquots of culture supernatants were analyzed by BioRads Cytokine Multiplex System.

Since HC Peptide 1 contains repeating collageneous sequences GLY-X-Y, it should be cleaved by a variety of proteases and peptidases to single amino acids outside of cells. When given orally, a small amount of the HC Peptide 1 may be absorbed into the blood stream (generally 5% orally administered proteins transverse the gastrointestinal mucosa and enter the blood unaltered). The above studies in the DRB1*0401 transgenic mice indicate that HC Peptide 1 is "processed" by the GALT resulting in increased IL-10 synthesis by Peyer's Patch cells (See Table VI).

2. Long Term Stability of HC Peptide 1

HC Peptide 1 was dissolved in phosphate buffered saline and stored at 4° C. for up to five months and then tested and compared in vitro with freshly prepared HC Peptide 1 to inhibit IFNγ production by RA patients PBMC stimulated by α1(II). As seen in Table VII, the HC Peptide 1 retained its ability to inhibit IFNγ production by α1(II) stimulated RA PBMC culture when stored for up to 5 months. This suggests that storage of HC peptide 1 during the clinical trial at 4° C. by patients will not lead to decreased biologic potency.

Acute Toxicity Studies on HC Peptide 1 NEOMPS Jul. 9, 2007 UT Lot #XS90-1211-042-29-06:

Eight DR1 transgenic mice (C57 BL/10 containing a human transgene for DR1) were studied in these acute toxicity studies. The four female litter mates were nine weeks old at the time the studies were initiated. Two female mice and two male mice were randomly assigned to the control group and two female and two male mice were randomly assigned to be treated with HC Peptide 1. Mice were gavaged once daily for seven days with 100 µl IV saline containing 100 µg HC Peptide1. Mice were weighed before treatment and every two days. Mice were examined daily for general healthy appearance, glossy coat, ruffling of hair, lethargy, ad lib behavior, shivering or vigor. At sacrifice on day 7, blood was collected for complete blood count and chemistries were performed by the Clinical Pathology Services, Charles River Laboratories, 251 Ballardvale Street, Wilmington, Mass. 01887. Food and water consumption were monitored in each cage. Liver and spleen were weighed at sacrifice of each mouse. Sections of liver, spleen, kidney, heart, lung, stomach, and small and large intestine, were placed in 10% formalin and processed for routine H and E sections by the Histology Laboratory at the Memphis VAMC. Mice were housed in an IACUC approved facility with 12 hours light and 12 hours darkness.

Results:

There were no differences in the general appearance or behavior of mice gavaged with 100× the proposed highest human dose of HC Peptide 1 compared to littermates gavaged with IV saline (See Table VIII). Changes in body weight over the six days mice were gavaged with 100× the human HC Peptide 1 dose were similar to mice gavaged with IV saline (See Table IX). Water and food consumption were similar between HC Peptide 1 treated and mice gavaged with IV saline (Table X). Upon sacrifice at day 7, the weight of livers and spleens were similar between mice gavaged with 100× the human dose of HC Peptide 1 and mice gavaged with IV saline (See Table XI). The complete blood counts (CBC) after 6 days gavage of DRB1*0401 transgenic mice with 100× the human HC Peptide 1 dose were similar to litter mates gavaged with IV saline. Plasma chemistries were similar in the DBA1*0401 transgenic mice gavaged with 100× the human dose of HC Peptide 1 compared to litter mates gavaged with IV saline.

Histologic assessment of internal organs revealed no difference in appearance of livers, spleens, kidneys, hearts or lungs in DRB1*0401 transgenic mice gavaged for six days with 100× human HC Peptide 1 dose compared to litter mates gavaged with IV saline.

TABLE VII

Stability of HC1 (APL A12) Stored at 4° C.

| | IFNγ Concentration in PBMC Supernatants (pg/ml) | | |
|---|---|---|---|
| | Time APL A12 Stored at 4° C. | | |
| Condition | 6 Days | 78 Days | 143 Days |
| PBS + PBS | 0 | N/A | N/A | N/A |
| PBS + α1(II) 50 µg/ml | 128 | N/A | N/A | N/A |
| A12 10 µg/ml + PBS | | 0 | 0 | 0 |
| A12 1 µg/ml + PBS | | 10 | 0 | 0 |
| A12 0.1 µg/ml + PBS | | 26 | 0 | 0 |
| A12 10 µg/ml + α1(II) 50 µg/ml | | 77 | 82 | 21 |
| A12 1 µg/ml + α1(II) 50 µg/ml | | 23 | 37 | 6 |
| A12 0.1 µg/ml + α1(II) 50 µg/ml | | 45 | 10 | 22 |

*A single lot of HC1 (APL A12) was purchased from NEOMPS (San Diego, CA) and stored at −70° C. in powder form. At 6, 78 and 143 days prior to addition to PBMC cultures from RA patient #154 previously determined to respond to APL A12 with reduction of IFNγ production when the PBMC were cultured with α1(II) + APL A12.

TABLE VIII

Effect of HC Peptide 1 on General Health of DRB1*0401

| | Healthy | Glossy Coat | Ruffling | Lethargy | Vigor | Ad Lib Behavior |
|---|---|---|---|---|---|---|
| Transgenic Mice HC Peptide 1 Treatment Male 1 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Male 2 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Female 5 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Female 6 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Control (Saline Treatment) Male 3 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Male 4 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Female 7 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |
| Female 8 | | | | | | |
| Day 1 | Yes | Yes | No | No | Yes | Normal |
| Day 2 | Yes | Yes | No | No | Yes | Normal |
| Day 3 | Yes | Yes | No | No | Yes | Normal |
| Day 4 | Yes | Yes | No | No | Yes | Normal |
| Day 5 | Yes | Yes | No | No | Yes | Normal |
| Day 6 | Yes | Yes | No | No | Yes | Normal |

TABLE IX

Weight (GMS) of Mice in Each Treatment Group*

| | Control (Saline Fed) Mice | | | |
|---|---|---|---|---|
| | Females | | Males | |
| | Mouse # | | | |
| | 7 | 8 | 3 | 4 |
| Time 0 | 18.3 | 18.9 | 21.8 | 21.8 |
| Day 2 | 18.8 | 19.3 | 21.7 | 22.0 |
| Day 4 | 18.4 | 19.0 | 21.2 | 21.2 |
| Day 6 | 18.9 | 19.5 | 21.1 | 21.3 |

| | HC Peptide 1 (100 μg) Fed | | | |
|---|---|---|---|---|
| | Females | | Males | |
| | Mouse # | | | |
| | 5 | 6 | 1 | 2 |
| Time 0 | 21.6 | 18.7 | 22.4 | 20.8 |
| Day 2 | 21.6 | 19.4 | 22.4 | 21.0 |
| Day 4 | 21.0 | 18.6 | 21.6 | 20.3 |
| Day 6 | 21.9 | 19.3 | 22.7 | 20.9 |

*Mice were weighed on a top-load balance on each day just before being gavaged.

TABLE X

Chow and Water Consumption per Cage Containing Two Mice Each for Each Treatment

| Days | Chow Consumed (GMS) | Water Consumed (MI) |
|---|---|---|
| | Cage 1 Male HC Peptide 1$R_x$ | Cage 1 Male HC Peptide 1$R_x$ |
| Days 1-2 | 13.3 | 15 |
| Days 3-4 | 10.5 | 10 |
| Days 5-6 | 14.4 | 15 |
| | 38.2 | 40 |
| | Cage 2 Male IV$R_x$ | Cage 2 Male IV$R_x$ |
| Days 1-2 | 18.5 | 12.5 |
| Days 3-4 | 16.4 | 9.5 |
| Days 5-6 | 15.8 | 13 |
| | 50.7 | 35 |
| | Cage 3 Female HC Peptide 1$R_x$ | Cage 3 Female HC Peptide 1$R_x$ |
| Days 1-2 | 15.7 | 12.5 |
| Days 3-4 | 14.2 | 9.5 |
| Days 5-6 | 15.3 | 13 |
| | 45.2 | 35 |
| | Cage 4 Female IV$R_x$ | Cage 3 Female IV$R_x$ |
| Days 1-2 | 25.3 | 15 |
| Days 3-4 | 12.6 | 10 |
| Days 5-6 | 12.3 | 15 |
| | 50.2 | 40 |

TABLE XI

Weight (GMS) of Livers and Spleens in Each Treatment Group

| | Control (Saline Fed) Mice | | | |
|---|---|---|---|---|
| | Females | | Males | |
| | Mouse # | | | |
| | 7 | 8 | 3 | 4 |
| Livers | 0.82 | 0.87 | 0.89 | 1.07 |
| Spleens | 0.07 | 0.10 | 0.06 | 0.07 |

| | HC Peptide 1 (100 μg) Fed Mice | | | |
|---|---|---|---|---|
| | Females | | Males | |
| | Mouse # | | | |
| | 5 | 6 | 1 | 2 |
| Livers | 0.99 | 0.87 | 1.14 | 0.9 |
| Spleens | 0.065 | 0.07 | 0.09 | 0.06 |

3. Use in Humans

APL A12 (HC Peptide 1) or other type II collagen-based APLs have to our knowledge never been administered to humans. A synthetic heat shock protein peptide was administered orally (dna JP1) to humans with RA with no apparent toxicity. As we reviewed in the background section, the subcutaneous administration of an APL of myelin basic protein to patients with MS was associated with some allergic reactions and or disease exacerbation. We believe our pre-screening of potential patients' PBMC in vitro with APL A12 might allow identification of RA patients whose arthritis might be exacerbated by the APL.

Treatment of Type I Diabetes Mellitus with Insulin B Chain APL:

Most type 1 diabetes mellitus patients exhibit Th1 response to the insulin B chain peptide epitope 9-23. An APL of human insulin B chain ($B_{9-23}$) wherein alanines were substituted for tyrosine at residue 15 and cysteine at residue 19 to give SHLVEALALVAGERG (SEQ ID NO: 4) (NBI-6024)) was given subcutaneously to adolescent and adult patients with recent onset of type 1 diabetes mellitus. Sixteen adolescent and 16 adult patients from six centers in the US were randomized into groups of five patients in which four received drug and one received placebo in a double-blinded fashion. Three of the adolescent and three of the adult groups received five subcutaneous injections of 0.1, 1 or 5 mg NBI-6024 at weeks 0, 2, 4, 6 and 8. There were no adverse events attributable to the APL. The purpose of the study in addition to assessing safety was to determine whether administration of this APL (NBI-6024) could suppress the pre-existing pathogenetic Th1 (IFNγ) response and induce a protective Th2 (IL-5) response to $B_{(9-23)}$ (and NBI-6024) in peripheral blood mononuclear cells (PBMC). PBMC expression of IFNγ and IL-5 were assessed by ELISPOT assay at weeks 0 (baseline), 2, 4, 6, 8, 14 and 26 after initiation of dosing with placebo or one of the three doses of the APL. A stimulation index (SI) was calculated for the IFNγ and IL-5 ELISPOT response by dividing the mean antigen induced spots (i.e. $B_{(9-23)}$ or NBI-6024) divided by the mean background (medium above) spots for each patient's sample and the mean patient SI per dosing groups (adolescents and adult cohorts combined, n=8) at each time point. They found that while the mean SI of IFNγ and IL-5 responses to $B_{(9-23)}$ and NBI-6024 for each cohort was variable during the 6-month assessment period, some SI responses of cohorts that received APL were significantly greater than those of the placebo groups. Using a mixed effects repeated measure statistical analysis there was one IFNγ response to $B_{(9-23)}$ that was significantly above (p=0.0002) the representative placebo cohort response which was the 5 mg cohort at week 15. In addition there were pronounced trends of elevated IL-5 responses to $B_{(9-23)}$ significant to $B_{(9-23)}$ the 1 mg cohort at week 4 (p=0.003), at to NBI-6024 by the 0.1 mg, cohort at week 26 (p=0.46) and by the 5 mg cohort at week 2 (p=0.032) IFNγ responses←NBI-6024 by all cohort that received APL were similar to those that received placebo. In spite of other longitudinal variability in the ELISPOT responses, this analysis strongly suggested that APL administration induced, predominantly Th2 responses to both the endogenous $B_{(9-23)}$ epitope and NBI-6024. In this study 29 of 31 patients genotyped for HLA alleles expressed the high-risk DR3 (DRB1*0301 and 0304) DR4 (DRB1*0401-0405), DQ2 (DQB1*0201) or DQ8 (DQB1*0302) alleles in which 21 patients expressed the DR4/DQ8 high-risk combination, 13 expressed the DR3/DQ2 high-risk combinations and seven expressed both high-risk combinations. Insulin $B_{(9-23)}$ and NBI-6024 bind the HLA-DQ8 haplotype.

Treatment of RA Patients with an Orally-Administered Synthetic Peptide (dnaJP1) Derived from Bacterial Heat Shock Protein:

Fifteen patients with RA of <5 years duration who had baseline T cell proliferation response to the dnaJP1 peptide ([O]QKRAAYDQ[U]YGHAAFE) (SEQ ID NO: 5) were treated for six months with orally administered dnaJP1 at doses of 0.25, 2.5 and 25 mg per day. The orally administered dnaJP1 peptide was well tolerated and no significant side effects occurred. This phase I study was not designed to assess efficacy but there was no worsening of arthritis in patients using dnaJP1. The dnaJP1, although not an altered peptide ligand but utilized natural heat shock protein sequence produced a switch in the cytokine profile from Th1 to Th2 manifested as reduced percentages of CD3+ cells secreting IFNγ and to reduced T cell proliferation to dnaJP1 and upregulation of IL-4 and IL-10 CD3+T cells. This study is highly relevant to the present IND application in that it demonstrates that a small synthetic peptide given orally that is MHC class II restructured in its interaction with antigen specific T cells is effective in down regulating a Th1 response and up regulating a Th2 response.

Treatment of Multiple Sclerosis with Myelin Basic Protein Based APL:

A major target for both humeral and cellular immune responses in patients with MS is a region of myelin basis protein (MBP) between residues 83 and 99. An APL called NBI-5788 was designed based on this epitope of MBP. A double-blind randomized, placebo-controlled Phase II trial was performed comparing doses of 16 weekly injections (subcutaneously) to assess safety, tolerability and influence on MRI lesion. The DSMB halted the study when it was observed that 13 out of 142 patients developed hypersensitivity reaction (9%). Analysis of 53 patients completing to double-blind phase of the study showed that the total volume and total number of enhancing lesions was reduced at the end of the trial compared with baseline in patients receiving the 5 mg weekly dose. Patients developed a Th2 response to the APL, a cross reaction with native MBP. There were no exacerbation of MS in this trial at this dose of NBI-5788. In open label, using 50 mg weekly injection of NBI-5788, 2 patients experienced exacerbation of MS with increased lesions on MRI and had enhanced responses to both NBI-5788 and native peptide $MBP_{(83-99)}$. A follow up study of patients in this clinical trial showed that NBI-5788 induced Th2 cytokine producing T cells that could be detected 2-4.5 years later by culturing PBMC with NBI-5788 or native $MBP_{(83-99)}$.

It should be understood that the foregoing disclosure emphasizes certain specific embodiments of the APLs For Treating Arthritis and that all modifications or alternatives equivalent thereto are within the spirit and scope of the APLs For Treating Arthritis as set forth in the appended claims. The combination of particular aspects of the various embodiments of the APLs For Treating Arthritis is included in the scope of this disclosure.

---

What is claimed and new and desired to be protected by Letters Patent of the United States is:

1. A therapeutic composition comprising an altered peptide ligand (APL) for treatment or inhibition of Rheumatoid Arthritis (RA) in patients in need thereof, wherein the APL comprises the amino acid sequence LGPKGQTGEBGIA-GAKGDQGPKGEBGPA (SEQ ID NO: 2).

2. The therapeutic composition of claim 1 in injectable form.

3. The therapeutic composition of claim 1 in oral form.

4. The therapeutic composition of claim 1 in a dose range effective to treat or inhibit RA in patients in need thereof.

5. The therapeutic composition of claim 4, wherein the dose range is from about 30 μg/day to about 1,000 μg/day.

6. The therapeutic composition of claim 5, wherein the dose is about 30 μg/day.

7. The therapeutic composition of claim 5, wherein the dose is about 300 μg/day.

8. The therapeutic composition of claim 5, wherein the dose is about 1,000 μg/day.

9. The therapeutic composition of claim 1, further comprising one or more compounds selected from carriers, solvents, and excipient.

10. A method of treating RA, comprising administering to a subject in need thereof the therapeutic composition of claim 2.

11. The composition of claim 1, further comprising a carbohydrate.

12. The method of claim 10, wherein administering is performed over a period of time.

13. The method of claim 12, wherein administering comprises one or more administrations within one day.

14. The method of claim 12, wherein administering comprises one or more administrations over a period of one or more days.

15. A method of inducing a T helper cell type 2 (Th2-type) cytokine secretion profile in a mammal, comprising administering a therapeutic amount of a peptide comprising SEQ ID NO: 2.

16. A method of generating functional T regulatory cells, the method comprising administering a therapeutic amount of a peptide sequence comprising SEQ ID NO: 2 to a RA patient.

* * * * *

SEQUENCE LISTING

```
<160> NUMBER OF SEQ ID NOS: 5

<210> SEQ ID NO 1
<211> LENGTH: 8
<212> TYPE: PRT
<213> ORGANISM: Homo sapiens

<400> SEQUENCE: 1

Phe Lys Gly Glu Gln Gly Pro Lys
1               5

<210> SEQ ID NO 2
<211> LENGTH: 28
<212> TYPE: PRT
<213> ORGANISM: Artificial Sequence
<220> FEATURE:
<223> OTHER INFORMATION: Synthetic peptide: HC Peptide1

<400> SEQUENCE: 2

Leu Gly Pro Lys Gly Gln Thr Gly Glu Asx Gly Ile Ala Gly Ala Lys
1               5                   10                  15

Gly Asp Gln Gly Pro Lys Gly Glu Asx Gly Pro Ala
            20                  25
```

```
<210> SEQ ID NO 3
<211> LENGTH: 28
<212> TYPE: PRT
<213> ORGANISM: Artificial Sequence
<220> FEATURE:
<223> OTHER INFORMATION: Synthetic peptide: APL A12
<220> FEATURE:
<221> NAME/KEY: misc_feature
<222> LOCATION: (25)..(25)
<223> OTHER INFORMATION: Xaa is hydroxyproline

<400> SEQUENCE: 3

Leu Gly Pro Lys Gly Gln Thr Gly Glu Asx Gly Ile Ala Gly Asn Lys
1               5                   10                  15

Gly Asp Gln Gly Pro Lys Gly Glu Xaa Gly Pro Ala
            20                  25

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide: APL of human insulin B chain

<400> SEQUENCE: 4

Ser His Leu Val Glu Ala Leu Ala Leu Val Ala Gly Glu Arg Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide: dnaJP1

<400> SEQUENCE: 5

Gln Lys Arg Ala Ala Tyr Asp Gln Tyr Gly His Ala Ala Phe Glu
1               5                   10                  15
```